(12) United States Patent
Wang et al.

(10) Patent No.: US 12,382,333 B2
(45) Date of Patent: Aug. 5, 2025

(54) METHODS FOR APPLICATION SPECIFIC ACCESS CONTROL

(71) Applicant: InterDigital Patent Holdings, Inc., Wilmington, DE (US)

(72) Inventors: Guanzhou Wang, Montreal (CA); Sudhir Kumar Baghel, Bridgewater, NJ (US); Li-Hsiang Sun, San Diego, CA (US); Saad Ahmad, Montreal (CA)

(73) Assignee: InterDigital Patent Holdings, Inc., Wilmington, DE (US)

( * ) Notice: Subject to any disclaimer, the term of this patent is extended or adjusted under 35 U.S.C. 154(b) by 0 days.

(21) Appl. No.: 17/953,612

(22) Filed: Sep. 27, 2022

(65) Prior Publication Data

US 2023/0018104 A1    Jan. 19, 2023

Related U.S. Application Data

(63) Continuation of application No. 14/914,569, filed as application No. PCT/US2014/052363 on Aug. 22, 2014, now Pat. No. 11,647,414.
(Continued)

(51) Int. Cl.
H04W 28/02    (2009.01)
A61B 10/00    (2006.01)
(Continued)

(52) U.S. Cl.
CPC ..... H04W 28/0268 (2013.01); A61B 10/0051 (2013.01); B01L 3/5023 (2013.01); H04W 4/50 (2018.02); B01L 2300/0609 (2013.01)

(58) Field of Classification Search
None
See application file for complete search history.

(56) References Cited

U.S. PATENT DOCUMENTS 8,341,395 B2    12/2012    Das et al.
8,826,444 B1    9/2014    Kalle
(Continued)

FOREIGN PATENT DOCUMENTS

CN    101888596 A    11/2010
CN    102687537 A    9/2012
(Continued)

OTHER PUBLICATIONS

"English Language Abstract", Japanese Patent Application No. JP2009-049543, Mar. 5, 2009, 1 page.
(Continued)

*Primary Examiner* — Pamit Kaur
(74) *Attorney, Agent, or Firm* — Flaster Greenberg, P.C.

(57) ABSTRACT

A method implemented on a UE includes determining an application class of an application, and permitting or barring access by the application to a communication network according to a comparison of the determined application with a rule to provide application class based access control. The application is classified into the determined application class. The application is classified into the determined application class by a home network. The application is classified into the determined application class by a 3GPP layer. The application is classified into the determined application class by a visited network. The visited network classifies the application into a further application class. The rule includes a list of applications for permitting or barring access by the applications according to the comparison of the determined application class with the rule.

20 Claims, 10 Drawing Sheets

Related U.S. Application Data

(60) Provisional application No. 61/872,272, filed on Aug. 30, 2013.

(51) Int. Cl.
 *B01L 3/00* (2006.01)
 *H04W 4/50* (2018.01)

(56) References Cited

U.S. PATENT DOCUMENTS

| | | | |
|---|---|---|---|
| 10,383,035 | B2 | 8/2019 | Sheng |
| 10,524,180 | B2 | 12/2019 | Hahn et al. |
| 2003/0064741 | A1 | 4/2003 | Silva et al. |
| 2006/0114832 | A1 | 6/2006 | Hamilton et al. |
| 2008/0232304 | A1 | 9/2008 | Mooney et al. |
| 2011/0171925 | A1 | 7/2011 | Faccin et al. |
| 2011/0310738 | A1 | 12/2011 | Lee et al. |
| 2012/0002545 | A1 | 1/2012 | Wwatfa et al. |
| 2012/0117140 | A1 | 5/2012 | Wang et al. |
| 2012/0124229 | A1 | 5/2012 | Sahu et al. |
| 2013/0029708 | A1 | 1/2013 | Fox et al. |
| 2013/0040597 | A1 | 2/2013 | Jang et al. |
| 2013/0201870 | A1 | 8/2013 | Gupta |
| 2013/0205366 | A1 | 8/2013 | Luna et al. |
| 2013/0215742 | A1 | 8/2013 | Sirotkin et al. |
| 2013/0267213 | A1 | 10/2013 | Hsu |
| 2013/0331099 | A1 | 12/2013 | Iwamura et al. |
| 2014/0010180 | A1 | 1/2014 | Lee et al. |
| 2014/0162647 | A1 | 6/2014 | Kato |
| 2014/0171096 | A1 | 6/2014 | Hwang et al. |
| 2014/0206373 | A1 | 7/2014 | Ljung |
| 2015/0036489 | A1* | 2/2015 | Rajadurai ........... H04L 47/2475 370/230 |
| 2015/0117213 | A1* | 4/2015 | Pinheiro ............... H04W 48/06 370/235 |
| 2015/0140956 | A1 | 5/2015 | Prewitt et al. |
| 2016/0014632 | A1 | 1/2016 | Siow et al. |
| 2016/0219493 | A1 | 7/2016 | Kim et al. |
| 2017/0013501 | A1 | 1/2017 | Kim et al. |
| 2017/0142560 | A1 | 5/2017 | Ryu et al. |
| 2017/0201871 | A1 | 7/2017 | Ryu et al. |
| 2018/0359681 | A1 | 12/2018 | Futaki |
| 2019/0159108 | A1 | 5/2019 | Lee et al. |
| 2019/0174395 | A1 | 6/2019 | Choe et al. |
| 2019/0223094 | A1 | 7/2019 | Ingale et al. |
| 2019/0320354 | A1 | 10/2019 | Kim et al. |
| 2019/0327663 | A1 | 10/2019 | Wirth et al. |
| 2019/0357120 | A1 | 11/2019 | Fu et al. |
| 2020/0052963 | A1 | 2/2020 | Kim et al. |
| 2020/0275344 | A1 | 8/2020 | Byun et al. |

FOREIGN PATENT DOCUMENTS

| | | |
|---|---|---|
| CN | 102893668 A | 1/2013 |
| CN | 105612788 A | 5/2016 |
| CN | 206096888 U | 4/2017 |
| EP | 2037636 A1 | 3/2009 |
| GB | 2465192 A | 5/2010 |
| JP | 2009049543 A | 3/2009 |
| JP | 2009267438 A | 11/2009 |
| JP | 2012175381 A | 9/2012 |
| WO | 2013020778 A1 | 2/2013 |
| WO | WO 2013/021532 A1 | 2/2013 |
| WO | WO 2014007592 A1 | 1/2014 |
| WO | 2015111929 A1 | 7/2015 |
| WO | 2017017890 A1 | 2/2017 |

OTHER PUBLICATIONS

"English Language Abstract", Japanese Patent Application No. JP 2009-267438, Nov. 12, 2009, 1 page.
"English Language Abstract", Chinese Patent Application No. CN 101888596, Nov. 17, 2017, 1 page.
"3rd Generation Partnership Project; Technical Specification Group Radio Access Network; Evolved Universal Terrestrial Radio Access (E-UTRA); Radio Resource Control (RRC); Protocol specification (Release 11)", 3GPP TS 36.331 V11.0.0, Jun. 2012, 302 pages.
"3rd Generation Partnership Project; Technical Specification Group Services and System Aspects; Architecture enhancements for non-3GPP accesses (Release 11)", 3GPP TS 23.402 V11.4.0, Sep. 2012, 252 pages.
"3rd Generation Partnership Project; Technical Specification Group Services and System Aspects; Service accessibility (Release 11)", 3GPP TS 22.011 V11.2.0, Dec. 2012, 26 pages.
"3rd Generation Partnership Project; Technical Specification Group Services and System Aspects; Study on Application Specific Congestion Control for Data Communication (Release 12)", 3GPP TR 22.806 V0.2.0, Nov. 2012, 8 pages.
"3rd Generation Partnership Project; Technical Specification Group Services and System Aspects; Study on Application specific congestion control for data communication (Release 13)", 3GPP TR 22.806 V0.3.0 (Aug. 2013), Aug. 27, 2013, 17 pages.
"3rd Generation Partnership Project; Technical Specification Group Services and System Aspects; Study on Service Specific Access Control (Release 11)", 3GPP TR 22.986 V11.0.0, Sep. 2012, 8 pages.
"3rd Generation Partnership Project; Technical Specification Group Services and System Aspects; System Enhancements for User Plane Congestion Management (Release 12)", 3GPP TR 23.705 V0.2.0, Feb. 2013, 9 pages.
"Change Request: Requirements for Application and Service Access Control", 3GPP Tdoc S1-133056, 3GPP TSG-SA WG1 Meeting #62, New Delhi, India, May 6-10, 2013, 4 pages.
"International Search Report and Written Opinion", International Application No. PCT/US2014/052363, Nov. 18, 2014, 5 pages.
"Prevention of mobile-originating signaling and/or data traffic of UEs in E-UTRAN in connected mode based on the criteria for the access barring mechanisms", 3GPPTdoc S1-131279, Change Request 3GPP TSG-SA WG1 Meeting #61, Prague, Czech Republic, Jan. 28-Feb. 1, 2013, 2 pages.
"Requirements applied to heavy congestion scenarios of ACDC", 3GPP Tdoc S1-131285 Change Request, 3GPP TSG-SA WG1 Meeting #61, Prague, Czech Republic, Jan. 28-Feb. 1, 2013, 2 pages.
"WID for Application and Service Access Control (ASAC)", 3GPP Tdoc TD SP-130124, 3GPP TSG SA Meeting #59, Vienna, Austria, Mar. 4-6, 2013, 5 pages.
"WID for Study on Application specific Congestion control for Data Communication (FS_ACDC)", 3GPP Tdoc Td SP-120546, 3GPP TSG SA Meeting #57, Chicago, USA, Sep. 10-12, 2012, 4 pages.
China Telecom, "Controlling ongoing service when ACDC activated", 3GPP Tdoc S1-134011, 3GPP TSG-SA WG1 Meeting #63, Zagreb, Croatia, Aug. 19-23, 2013, 3 pages.
3rd Generation Partnership Project (3GPP); 3GPP TS 22.011, V15.1.0 , "Service Accessibility (Release 15)", Technical Specification Group Services and System Aspects, Jun. 2017, 32 pages.
ITU-R M.2083-0 , "IMT Vision—Framework and overall objectives of the future development of IMT for 2020 and beyond; M Series Mobile, radio determination, amateur and related satellite services", International Telecommunication Union, Recommendation ITUR, Sep. 2015, 21 pages.
3rd Generation Partnership Project (3GPP); R2-1706505 , "Access Control for NR", Ericsson, 3GPP TSG-RAN WG2 NR#2, Jun. 27-29, 2017, 5 pages.
3rd Generation Partnership Project (3GPP); R2-1706509 , "Signalling of Access Control Parameters", Ericsson, 3GPP TSG-RAN WG2 NR#2, Jun. 27-29, 2017, 6 pages.
3rd Generation Partnership Project (3GPP); R2-1706771 , "Basic Access Control in NR", Huawei, HiSilicon, 3GPP TSG-RAN WG2 NRAdhoc#2, Jun. 27-29, 2017, 6 pages.
3rd Generation Partnership Project (3GPP); R2-1707046 , "5G Access Control Mechanism", Intel Corporation, 3GPP TSG RAN WG2 AdHoc Meeting, Jun. 27-29, 2017, 8 pages.

* cited by examiner

METHODS FOR APPLICATION SPECIFIC ACCESS CONTROL

CROSS REFERENCE TO RELATED APPLICATIONS

This application is a continuation of the U.S. Non-Provisional patent application Ser. No. 14/914,569, filed Feb. 25, 2016, which is the National Stage Application filed under 35 U.S.C. 371 of International Application No. PCT/US2014/052363, filed Aug. 22, 2014, which claims the benefit of U.S. Provisional Patent Application No. 61/872,272, filed Aug. 30, 2013, the contents of each of which are incorporated by reference herein.

FIELD OF INVENTION

The present invention relates to the field of wireless communication.

BACKGROUND

The network congestion caused by smart phone applications has been observed in current 3G and 4G networks. This situation may continue to be exacerbated as more and more bandwidth consuming applications become popular. Various access control mechanisms for combating the congestion may be known in the art, for example, access class barring (ACB), extended access barring (EAB), domain specific access control (DSAC), service specific access control (SSAC), etc. However, these mechanisms work in similar ways to bar a percentage of the user equipment (UE) from accessing the network, without differentiating between various applications. If a UE is barred by ACB or EAB, all its applications may be barred, even though some of them may not contribute to the congestion. In many situations, the operators may still need to allow access for almost all of the UEs for emergency or higher priority services, but bar a few resource consuming and low priority applications. There are several examples of such situations.

In disaster scenarios, many users may use services like disaster message board (DMB) or disaster voice messaging (DVM) to confirm the safety of their families or friends. To make sure these services are not disrupted by possible network congestion, the operators may bar the access of other low priority applications to free up the network resources.

In areas where high user density is inevitable and cell congestion is more likely, like metro stations, concerts or sporting events, an operator may want to bar a few low priority and resource consuming applications. This may prevent basic services such as voice and messaging from being affected.

When public safety missions are carried out in an area, more resources may be required. Some applications may therefore be barred in order to relieve the network while the basic services for other ordinary users can still continue. In order to address such issues, a study item SP-120546, WID proposal for application specific congestion control for data communication (FS_ACDC), was approved in SA #57. Later a work item SP-130124, WID proposal for application and service access control was approved in SA #59. The objective of these work items was to specify service requirements for systems that would be able to allow/prohibit the communication initiation of particular applications defined by the operators and subject to regional regulations. The requirements were intended to prevent/mitigate overload of the access network and/or the core network before/under situation defined by operators, e.g., in heavy congestion or disaster case. Furthermore, 3rd generation partnership project (3GPP) specifications have already defined several access control mechanisms.

For example, ACB has been defined. In ABC, at the time of subscription one or more access classes (AC) may be allocated to a subscriber, and stored in a universal subscriber identity module (USIM). Normal UEs may be randomly assigned an AC between 0~9. Some special UEs could be assigned a higher priority, e.g., AC 11~15. ACB information is broadcast in the system information, which basically controls the mean access barring time, and the percentage of the barred accesses. When a UE tries to initiate an access, it will try to draw a random number among (0, 1) and compare the random number against the ACB factor, which is part of the broadcasted ACB information. If the random number is greater than the ACB factor, then the access will be barred for a period corresponding to the calculated mean barring time.

EAB may be targeted only at those UEs which may be configured to be subject to EAB control. Usually these UEs may be of lower priority or delay tolerant, for example, machine type communications (MTC) devices. Before initiating an access, the non access stratum (NAS) may determine whether the access is subject to EAB control based on a few criteria. The criteria could include the UE's roaming category, the nature of the access, whether the UE is of special AC (11~15), etc. If it is, the NAS will compare the UE's AC with a broadcasted EAB barring bitmap, where each bit represents the barring status of an AC (0~9). As distinguished from ACB, there is no barring factor or barring time defined in the EAB parameters.

SSAC is based on the ACB with a different set of dedicated SSAC barring parameters. The dedicated SSAC barring parameters can differentiate the multimedia telephony service (MMTEL) voice service and the MMTEL video service with different barring factors and barring times. Based on broadcasted SSAC barring configurations and a UE's AC, the UE can determine the real barring parameters and inform the upper service layer. The service layer, before initiating the service, can draw a random number and compare it against the barring parameters in order to decide whether the service is barred.

Referring now to FIG. 2, there is shown a high level view of a possible embodiment of user plane congestion (UPCON) management system 200. UPCON management may be performed within UPCON management system 200 according to a 3GPP work item listed below. The UPCON may occur in radio access network (RAN) 212 when the demand for RAN resources exceeds the available RAN capacity, or on network interfaces (e.g., S1-U) when the data throughput exceeds the available bandwidth. This may be detected in congestion prediction/detection 1. The congestion prediction/detection can be applied to RAN 212. Solutions for the congestion in system 200 may include reporting RAN congestion by congestion indication 2. Solutions may also include RAN 212 or core network (CN) 208 based congestion mitigation, for example, by CN based congestion mitigation 4, service/QoS information for RAN based congestion mitigation 5a, and RAN-based congestion mitigation 5b. Application and service access control (ASAC) and UPCON management may be similar in that they may both attempt to mitigate the congestion by reducing some application traffic. The difference is that ASAC blocks specific applications from accessing the network, while the UPCON management only throttles the application traffic.

SUMMARY

A method implemented on a UE includes determining an application class of an application, and permitting or barring access by the application to a communication network according to a comparison of the determined application with a rule to provide application class based access control. The application is classified into the determined class. The application is classified into the determined class by a home network. The application is classified into the determined class by a 3GPP layer. The application is classified into the determined class by a visited network. The visited network classifies the application into a further application class. The rule includes a list of applications, and permitting access by the applications of the list of applications according to the comparison of the determined application class with the rule is also provided. A period of time the rule is active, and a time at which the rule becomes active are provided. The rule is determined according to a level of congestion of a communication network. The level of congestion is determined according to a system information block (SIB). The rule includes at least one access class identifier for indicating an AC that is subject to the rule. A communication network updates the rule. A communication network updates the rule according to a level of congestion in the communication network.

A general UE model for ASAC may be based on application class control. The model may include a method for configuring AC identification information and AC based ASAC rules in the UE. Specifically, a self-trained application class identification method may be used. Furthermore, a gradual and graceful ASAC deactivation method may gradually permit access of the barred applications/application classes according to a different level of congestion. Methods for a UE to recognize an application/application class that caused the paging so the ASAC rules may also be applied to the mobile telecommunication (MT) services. Additionally, methods may be applied to a mobility management entity (MME)/eNB in order to filter any paging caused by barred applications.

The methods for linking the ASAC may be associated with individual operators in a RAN shared environment, and methods for the host operator to request hosted operators to change ASAC settings may be provided. Methods may configure multiple indexed access network discovery and selection function (ANDSF) policies in the UE for congestion control, and the network may use the index to activate a specific policy. Furthermore, methods may prevent applications/services from originating in connected UEs by adding a block attribute to traffic flow template (TFT) packet filters. Additionally, methods may apply ASAC for device-to-device (D2D) communications. It will be understood that in the context of ANDSF the term policy may be commonly used, while in the context of ASAC the term rules may be used. Thus, the terms policy and rules may be used interchangeable herein.

BRIEF DESCRIPTION OF THE DRAWINGS

A more detailed understanding may be had from the detailed description below, given by way of example in conjunction with drawings appended hereto. Figures in such drawings, like the detailed description, may be examples. As such, the Figures and the detailed description are not to be considered limiting, and other equally effective examples are possible and likely. Furthermore, like reference numerals in the Figures indicate like elements, and wherein.

DETAILED DESCRIPTION OF THE PREFERRED EMBODIMENT

In the following detailed description, numerous specific details are set forth to provide a thorough understanding of embodiments and/or examples disclosed herein. However, it will be understood that such embodiments and examples may be practiced without some or all of the specific details set forth herein. In other instances, well known methods, procedures, components and circuits have not been described in detail, so as not to obscure the following description. Further, embodiments and examples not specifically described herein may be practiced in lieu of, or in combination with, the embodiments and other examples disclosed herein.

Example Architecture

When referred to herein, the terms "user equipment" and its abbreviation "UE" may mean (i) a wireless transmit and/or receive unit (WTRU), such as described infra; (ii) any of a number of embodiments of a WTRU, such as described infra; (iii) a wireless capable and/or wired capable (e.g., capable of being tethered) device configured with, inter alia, some or all structures and functionality of a WTRU, such as described infra; (iii) a wireless capable and/or wired capable device configured with less than all structures and functionality of a WTRU, such as described infra; or (iv) the like. Details of an example WTRU, which may be representative of any UE recited herein, are provided below with respect to FIGS. 1A-1C.

When referred to herein, the terms "evolved NodeB" and its abbreviations "eNB" and "eNodeB" may mean (i) a base station, such as described infra; (ii) any of a number of embodiments of a base station, such as described infra; (iii) a device configured with, inter alia, some or all structures and functionality of a base station or eNB, such as described infra; (iii) a device configured with less than all structures and functionality of a base station or eNB, such as described infra; or (iv) the like. Details of an example eNB, which may be representative of any eNB recited herein, are provided below with respect to FIGS. 1A-1C.

When referred to herein, the terms "mobility management entity" and its abbreviation "MME" may mean (i) an MME, such as described infra; (ii) an MME according to a 3GPP LTE release; (iii) an MME according to a 3GPP LTE release modified, extended and/or enhanced according to the description that follows; (iii) a device configured with, inter alia, some or all structures and functionality of any of the aforementioned MMEs; (iv) a device configured with less than all structures and functionality of any of the MMEs of (i) and (ii) above; or (iv) the like. Details of an example MME, which may be representative of any MME recited herein, are provided below with respect to FIGS. 1A-1C.

Figure 1A:
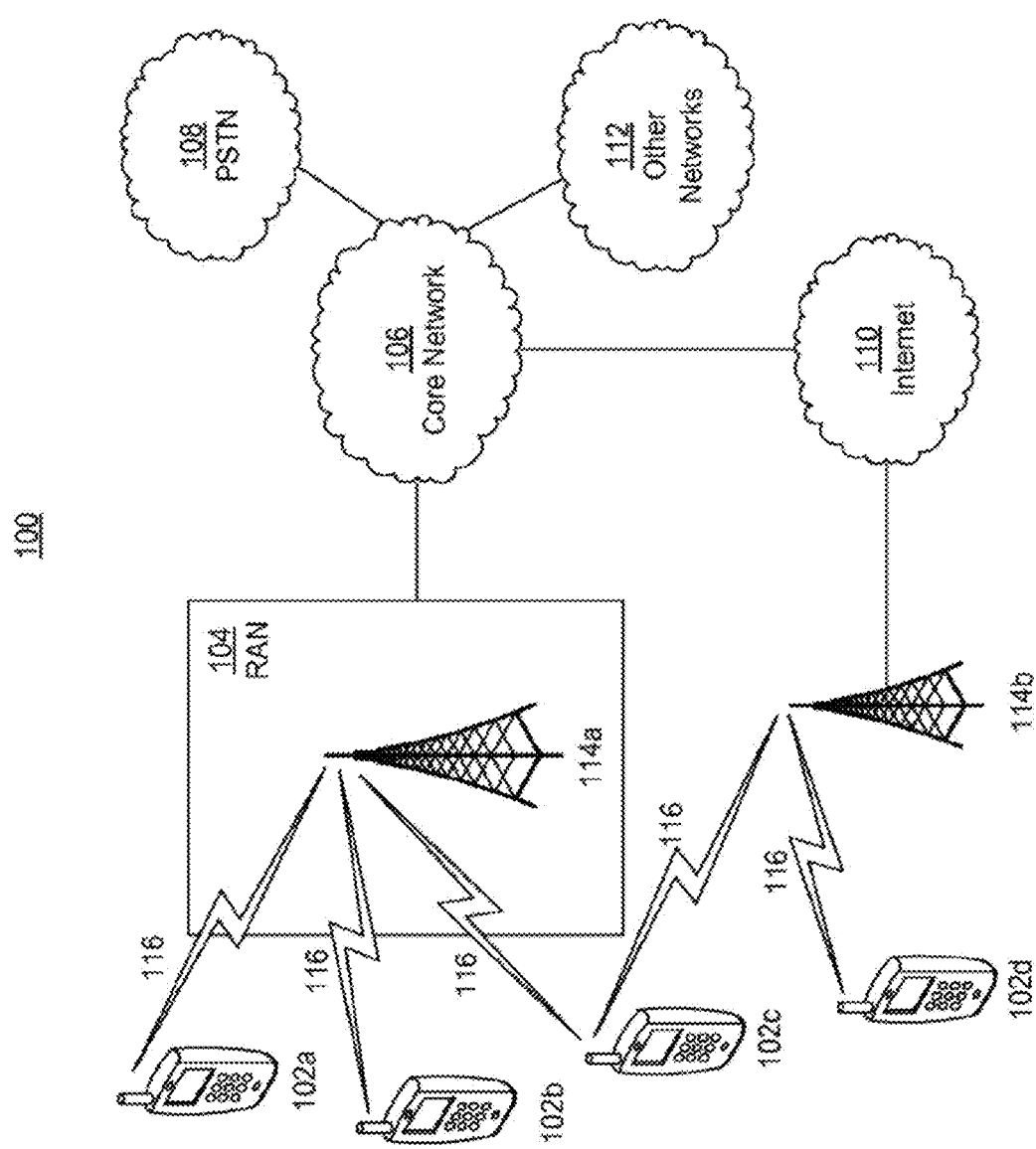
FIG. 1A is a diagram of an example communications system in which one or more disclosed embodiments may be implemented.

FIG. 1A is a diagram of an example communications system 1100 in which one or more disclosed embodiments may be implemented. The communications system 100 may be a multiple access system that provides content, such as voice, data, video, messaging, broadcast, etc., to multiple wireless users. The communications system 100 may enable multiple wireless users to access such content through the sharing of system resources, including wireless bandwidth. For example, the communications systems 100 may employ one or more channel access methods, such as code division multiple access (CDMA), time division multiple access (TDMA), frequency division multiple access (FDMA), orthogonal FDMA (OFDMA), single carrier FDMA (SC-FDMA), and the like.

As shown in FIG. 1A, the communications system 100 may include wireless transmit/receive units (WTRUs) 102a, 102b, 102c, 102d, a radio access network (RAN) 104, a core network 106, a public switched telephone network (PSTN) 108, the Internet 110, and other networks 112, though it will be appreciated that the disclosed embodiments contemplate any number of WTRUs, base stations, networks, and/or network elements. Each of the WTRUs 102a, 102b, 102c, 102d may be any type of device configured to operate and/or communicate in a wireless environment. By way of example, the WTRUs 102a, 102b, 102c, 102d may be configured to transmit and/or receive wireless signals and may include user equipment (UE), a mobile station, a fixed or mobile subscriber unit, a pager, a cellular telephone, a personal digital assistant (PDA), a Smartphone, a laptop, a netbook, a personal computer, a tablet computer, a wireless sensor, consumer electronics, and the like.

The communications systems 100 may also include a base station 114a and a base station 114b. Each of the base stations 114a, 114b may be any type of device configured to wirelessly interface with at least one of the WTRUs 102a, 102b, 102c, 102d to facilitate access to one or more communication networks, such as the core network 106, the Internet 110, and/or the networks 112. By way of example, the base stations 114a, 114b may be a base transceiver station (BTS), a NodeB, an eNodeB, a Home NodeB, a Home eNodeB, a site controller, an access point (AP), a wireless router, and the like. While the base stations 114a, 114b are each depicted as a single element, it will be appreciated that the base stations 114a, 114b may include any number of interconnected base stations and/or network elements.

The base station 114a may be part of the RAN 104, which may also include other base stations and/or network elements (not shown), such as a base station controller (BSC), a radio network controller (RNC), relay nodes, etc. The base station 114a and/or the base station 114b may be configured to transmit and/or receive wireless signals within a particular geographic region, which may be referred to as a cell (not shown). The cell may further be divided into cell sectors. For example, the cell associated with the base station 114a may be divided into three sectors. Thus, in one embodiment, the base station 114a may include three transceivers, i.e., one for each sector of the cell. In another embodiment, the base station 114a may employ multiple-input multiple output (MIMO) technology and, therefore, may utilize multiple transceivers for each sector of the cell.

The base stations 114a, 114b may communicate with one or more of the WTRUs 102a, 102b, 102c, 102d over an air interface 116, which may be any suitable wireless communication link (e.g., radio frequency (RF), microwave, infrared (IR), ultraviolet (UV), visible light, etc.). The air interface 116 may be established using any suitable radio access technology (RAT).

More specifically, as noted above, the communications system 100 may be a multiple access system and may employ one or more channel access schemes, such as CDMA, TDMA, FDMA, OFDMA, SC-FDMA, and the like. For example, the base station 114a in the RAN 104 and the WTRUs 102a, 102b, 102c may implement a radio technology such as universal mobile telecommunications system (UMTS) terrestrial radio access (UTRA), which may establish the air interface 116 using wideband CDMA (WCDMA). WCDMA may include communication protocols such as high speed packet access (HSPA) and/or evolved HSPA (HSPA+). HSPA may include high speed downlink packet access (HSDPA) and/or high speed uplink packet access (HSUPA).

In another embodiment, the base station 114a and the WTRUs 102a, 102b, 102c may implement a radio technology such as Evolved UMTS Terrestrial Radio Access (E-UTRA), which may establish the air interface 116 using Long Term Evolution (LTE) and/or LTE-Advanced (LTE-A).

In other embodiments, the base station 114a and the WTRUs 102a, 102b, 102c may implement radio technologies such as IEEE 802.16 (i.e., worldwide interoperability for microwave access (WiMAX)), CDMA2000, CDMA2000 1x, CDMA2000 EV-DO, Interim Standard 2000 (IS-2000), Interim Standard 95 (IS-95), Interim Standard 856 (IS-856), global system for mobile communications (GSM), Enhanced Data rates for GSM evolution (EDGE), GSM EDGE (GERAN), and the like.

The base station 114b in FIG. 1A may be a wireless router, Home Node B, Home eNodeB, or access point, for example, and may utilize any suitable RAT for facilitating wireless connectivity in a localized area, such as a place of business, a home, a vehicle, a campus, and the like. In one embodiment, the base station 114b and the WTRUs 102c, 102d may implement a radio technology such as IEEE 802.11 to establish a wireless local area network (WLAN). In another embodiment, the base station 114b and the WTRUs 102c, 102d may implement a radio technology such as IEEE 802.15 to establish a wireless personal area network (WPAN). In yet another embodiment, the base station 114b and the WTRUs 102c, 102d may utilize a cellular based RAT (e.g., WCDMA, CDMA2000, GSM, LTE, LTE-A, etc.) to establish a picocell or femtocell. As shown in FIG. 1A, the base station 114b may have a direct connection to the Internet 110. Thus, the base station 114b may not be required to access the Internet 110 via the core network 106.

The RAN 104 may be in communication with the core network 106, which may be any type of network configured to provide voice, data, applications, and/or voice over internet protocol (VoIP) services to one or more of the WTRUs 102a, 102b, 102c, 102d. For example, the core network 106 may provide call control, billing services, mobile location based services, prepaid calling, Internet connectivity, video distribution, etc., and/or perform high level security functions, such as user authentication. Although not shown in FIG. 1A, it will be appreciated that the RAN 104 and/or the core network 106 may be in direct or indirect communication with other RANs that employ the same RAT as the RAN 104 or a different RAT. For example, in addition to being connected to the RAN 104, which may be utilizing an E-UTRA radio technology, the core network 106 may also be in communication with another RAN (not shown) employing a GSM radio technology.

The core network 106 may also serve as a gateway for the WTRUs 102a, 102b, 102c, 102d to access the PSTN 108, the Internet 110, and/or other networks 112. The PSTN 108 may include circuit switched telephone networks that provide plain old telephone service (POTS). The Internet 110 may include a global system of interconnected computer networks and devices that use common communication protocols, such as the Transmission Control Protocol (TCP), user datagram protocol (UDP) and the Internet Protocol (IP) in the TCP/IP internet protocol suite. The networks 112 may include wired or wireless communications networks owned and/or operated by other service providers. For example, the networks 112 may include another core network connected to one or more RANs, which may employ the same RAT as the RAN 104 or a different RAT.

Some or all of the WTRUs 102a, 102b, 102c, 102d in the communications system 100 may include multimode capabilities, i.e., the WTRUs 102a, 102b, 102c, 102d may include multiple transceivers for communicating with different wireless networks over different wireless links. For example, the WTRU 102c shown in FIG. 1A may be configured to communicate with the base station 114a, which may employ a cellular based radio technology, and with the base station 114b, which may employ an IEEE 802 radio technology.

Figure 1B:
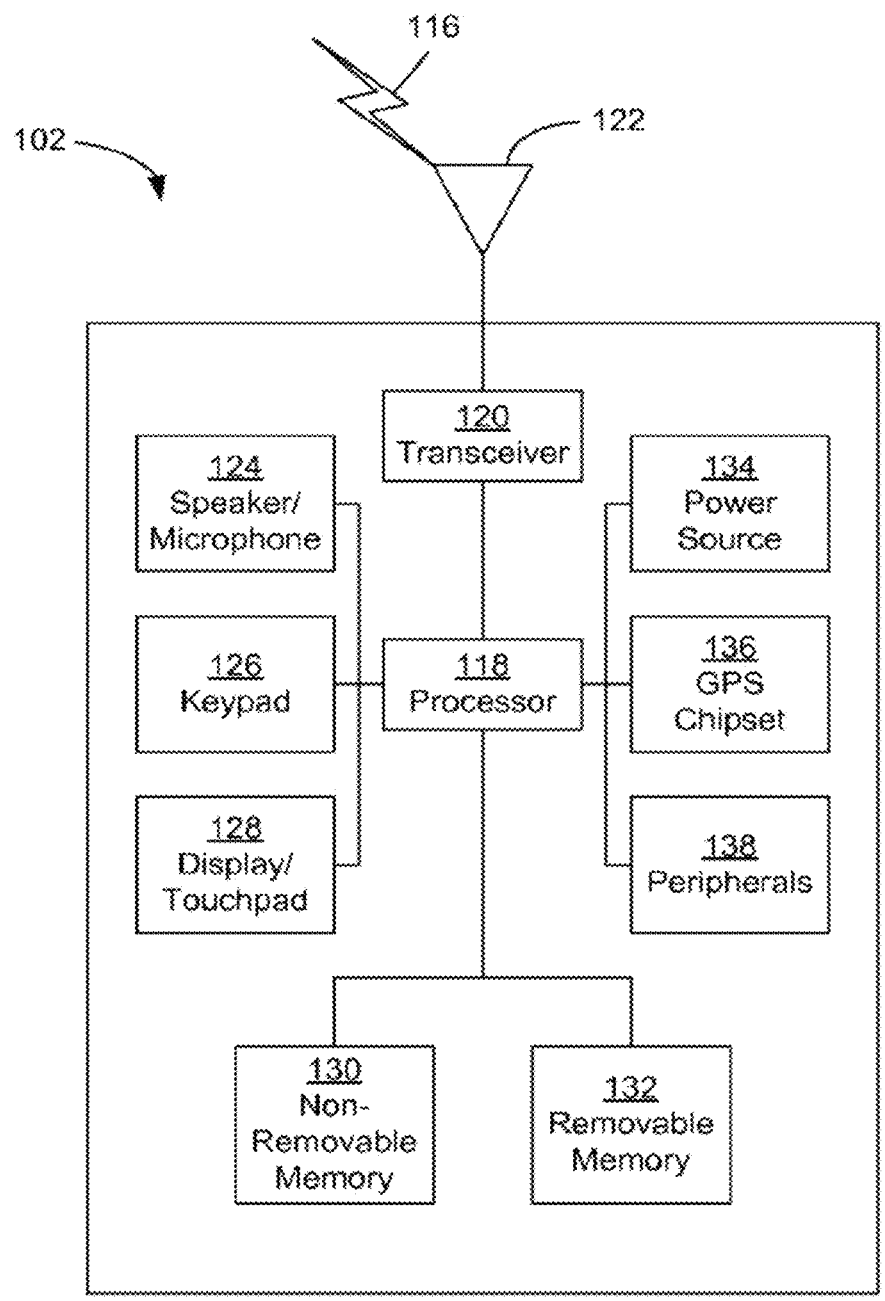
FIG. 1B is a system diagram of an example wireless transmit/receive unit (WTRU) that may be used within the communications system illustrated in FIG. 1A.

FIG. 1B is a system diagram of an example WTRU 102. As shown in FIG. 1B, the WTRU 102 may include a processor 118, a transceiver 120, a transmit/receive element 122, a speaker/microphone 124, a keypad 126, a display/touchpad 128, no removable memory 19, removable memory 132, a power source 134, a global positioning system (GPS) chipset 136, and other peripherals 138. It will be appreciated that the WTRU 102 may include any sub combination of the foregoing elements while remaining consistent with an embodiment.

The processor 118 may be a general purpose processor, a special purpose processor, a conventional processor, a digital signal processor (DSP), a plurality of microprocessors, one or more microprocessors in association with a DSP core, a controller, a microcontroller, application specific integrated circuits (ASICs), field programmable gate array (FPGA) circuits, any other type of integrated circuit (IC), a state machine, and the like. The processor 118 may perform signal coding, data processing, power control, input/output processing, and/or any other functionality that enables the WTRU 102 to operate in a wireless environment. The processor 118 may be coupled to the transceiver 120, which may be coupled to the transmit/receive element 122. While FIG. 1B depicts the processor 118 and the transceiver 120 as separate components, it will be appreciated that the processor 118 and the transceiver 120 may be integrated together in an electronic package or chip.

The transmit/receive element 122 may be configured to transmit signals to, or receive signals from, a base station (e.g., the base station 114a) over the air interface 116. For example, in one embodiment, the transmit/receive element 122 may be an antenna configured to transmit and/or receive RF signals. In another embodiment, the transmit/receive element 122 may be an emitter/detector configured to transmit and/or receive IR, UV, or visible light signals, for example. In yet another embodiment, the transmit/receive element 122 may be configured to transmit and receive both RF and light signals. It will be appreciated that the transmit/receive element 122 may be configured to transmit and/or receive any combination of wireless signals.

In addition, although the transmit/receive element 122 is depicted in FIG. 1B as a single element, the WTRU 102 may include any number of transmit/receive elements 122. More specifically, the WTRU 102 may employ MIMO technology. Thus, in one embodiment, the WTRU 102 may include two or more transmit/receive elements 122 (e.g., multiple antennas) for transmitting and receiving wireless signals over the air interface 116.

The transceiver 120 may be configured to modulate the signals that are to be transmitted by the transmit/receive element 122 and to demodulate the signals that are received by the transmit/receive element 122. As noted above, the WTRU 102 may have multimode capabilities. Thus, the transceiver 120 may include multiple transceivers for enabling the WTRU 102 to communicate via multiple RATs, such as UTRA and IEEE 802.11, for example.

The processor 118 of the WTRU 102 may be coupled to, and may receive user input data from, the speaker/microphone 124, the keypad 126, and/or the display/touchpad 128 (e.g., a liquid crystal display (LCD) display unit or organic light emitting diode (OLED) display unit). The processor 118 may also output user data to the speaker/microphone 124, the keypad 126, and/or the display/touchpad 128. In addition, the processor 118 may access information from, and store data in, any type of suitable memory, such as the no removable memory 130 and/or the removable memory 132. The no removable memory 19 may include random access memory (RAM), read only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the WTRU 102, such as on a server or a home computer (not shown).

The processor 118 may receive power from the power source 134, and may be configured to distribute and/or control the power to the other components in the WTRU 102. The power source 134 may be any suitable device for powering the WTRU 102. For example, the power source 134 may include one or more dry cell batteries (e.g., nickel cadmium (NiCd), nickel zinc (NiZn), nickel metal hydride (NiMH), lithium ion (Li-ion), etc.), solar cells, fuel cells, and the like.

The processor 118 may also be coupled to the GPS chipset 136, which may be configured to provide location information (e.g., longitude and latitude) regarding the current location of the WTRU 102. In addition to, or in lieu of, the information from the GPS chipset 136, the WTRU 102 may receive location information over the air interface 116 from a base station (e.g., base stations 114a, 114b) and/or determine its location based on the timing of the signals being received from two or more nearby base stations. It will be appreciated that the WTRU 102 may acquire location information by way of any suitable location determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include an accelerometer, an e-compass, a satellite transceiver, a digital camera (for photographs or video), a universal serial bus (USB) port, a vibration device, a television transceiver, a hands free headset, a Bluetooth® module, a frequency modulated (FM) radio unit, a digital music player, a media player, a video game player module, an Internet browser, and the like.

Figure 1C:
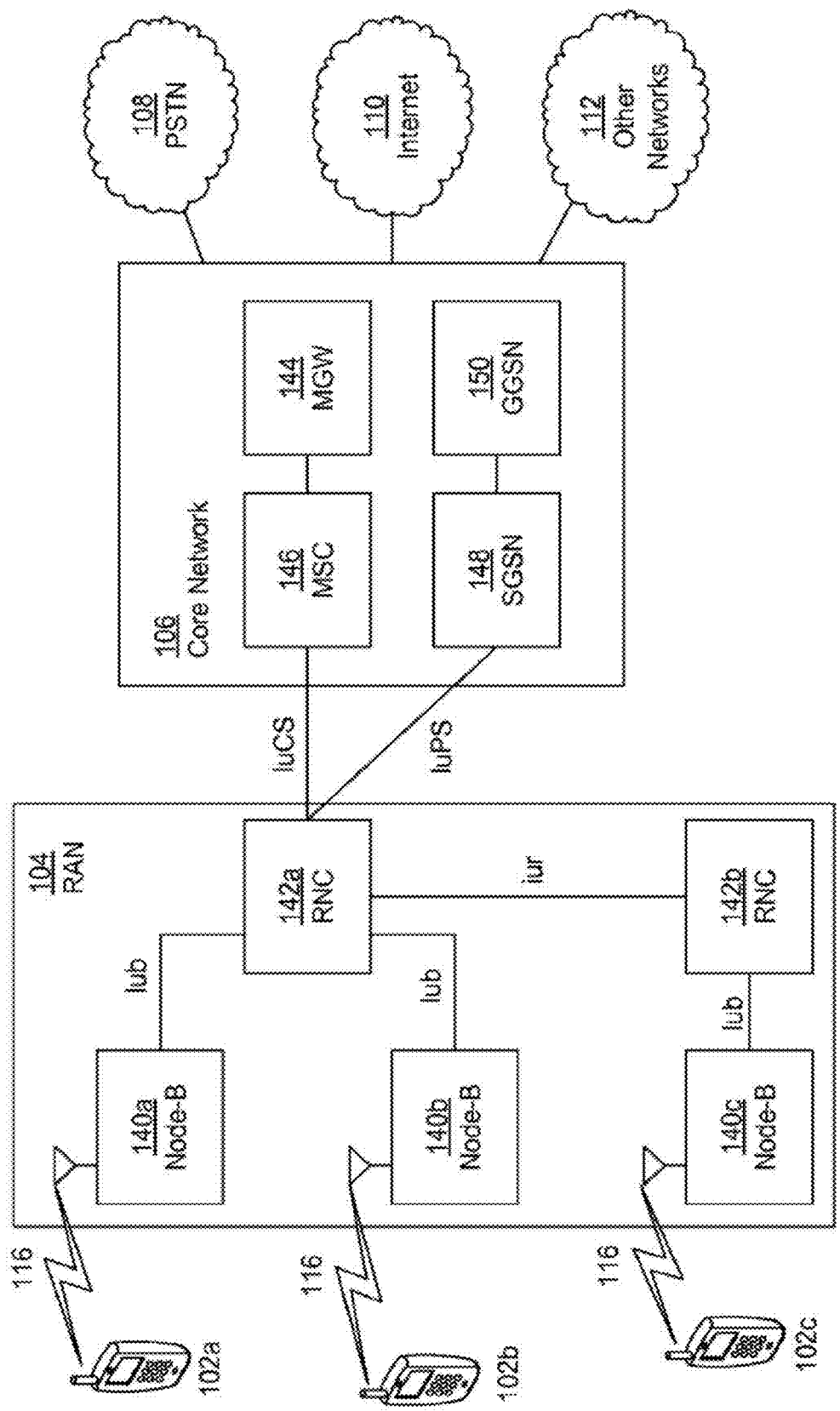
FIG. 1C is a system diagram of an example radio access network and an example core network that may be used within the communications system illustrated in FIG. 1A.

FIG. 1C is a system diagram of the RAN 104 and the core network 106 according to an embodiment. As noted above, the RAN 104 may use UTRA radio technology to communicate with the WTRUs 102a, 102b, and 102c over the air interface 116. The RAN 104 may also be in communication with the core network 106. As shown in FIG. 1C, the RAN 104 may include NodeBs 140a, 140b, 140c, which may each include one or more transceivers for communicating with the WTRUs 102a, 102b, 102c over the air interface 116. The NodeBs 140a, 140b, 140c may each be associated with a particular cell (not shown) within the RAN 104. The RAN 104 may also include RNCs 142a, 142b. It will be appreciated that the RAN 104 may include any number of NodeBs and RNCs while remaining consistent with an embodiment.

As shown in FIG. 1C, the NodeBs 140a, 140b may be in communication with the RNC 142a. Additionally, the NodeB 140c may be in communication with the RNC 142b. The NodeBs 140a, 140b, 140c may communicate with the respective RNCs 142a, 142b via an Iub interface. The RNCs 142a, 142b may be in communication with one another via an Iur interface. Each of the RNCs 142a, 142b may be configured to control the respective NodeBs 140a, 140b, 140c to which it is connected. In addition, each of the RNCs 142a, 142b may be configured to carry out or support other functionality, such as outer loop power control, load control, admission control, packet scheduling, handover control, macrodiversity, security functions, data encryption, and the like.

The core network 106 shown in FIG. 1C may include a media gateway (MGW) 144, a mobile switching center (MSC) 146, a serving GPRS support node (SGSN) 148, and/or a gateway GPRS support node (GGSN) 150. While each of the foregoing elements are depicted as part of the core network 106, it will be appreciated that any one of these elements may be owned and/or operated by an entity other than the core network operator.

The RNC 142a in the RAN 104 may be connected to the MSC 146 in the core network 106 via an IuCS interface. The MSC 146 may be connected to the MGW 144. The MSC 146 and the MGW 144 may provide the WTRUs 102a, 102b, 102c with access to circuit switched networks, such as the PSTN 108, to facilitate communications between the WTRUs 102a, 102b, 102c and traditional land line communications devices.

The RNC 142a in the RAN 104 may also be connected to the SGSN 148 in the core network 106 via an IuPS interface. The SGSN 148 may be connected to the GGSN 150. The SGSN 148 and the GGSN 150 may provide the WTRUs 102a, 102b, 102c with access to packet switched networks, such as the Internet 110, to facilitate communications between and the WTRUs 102a, 102b, 102c and IP enabled devices.

As noted above, the core network 106 may also be connected to the networks 112, which may include other wired or wireless networks that are owned and/or operated by other service providers.

Figure 1D:
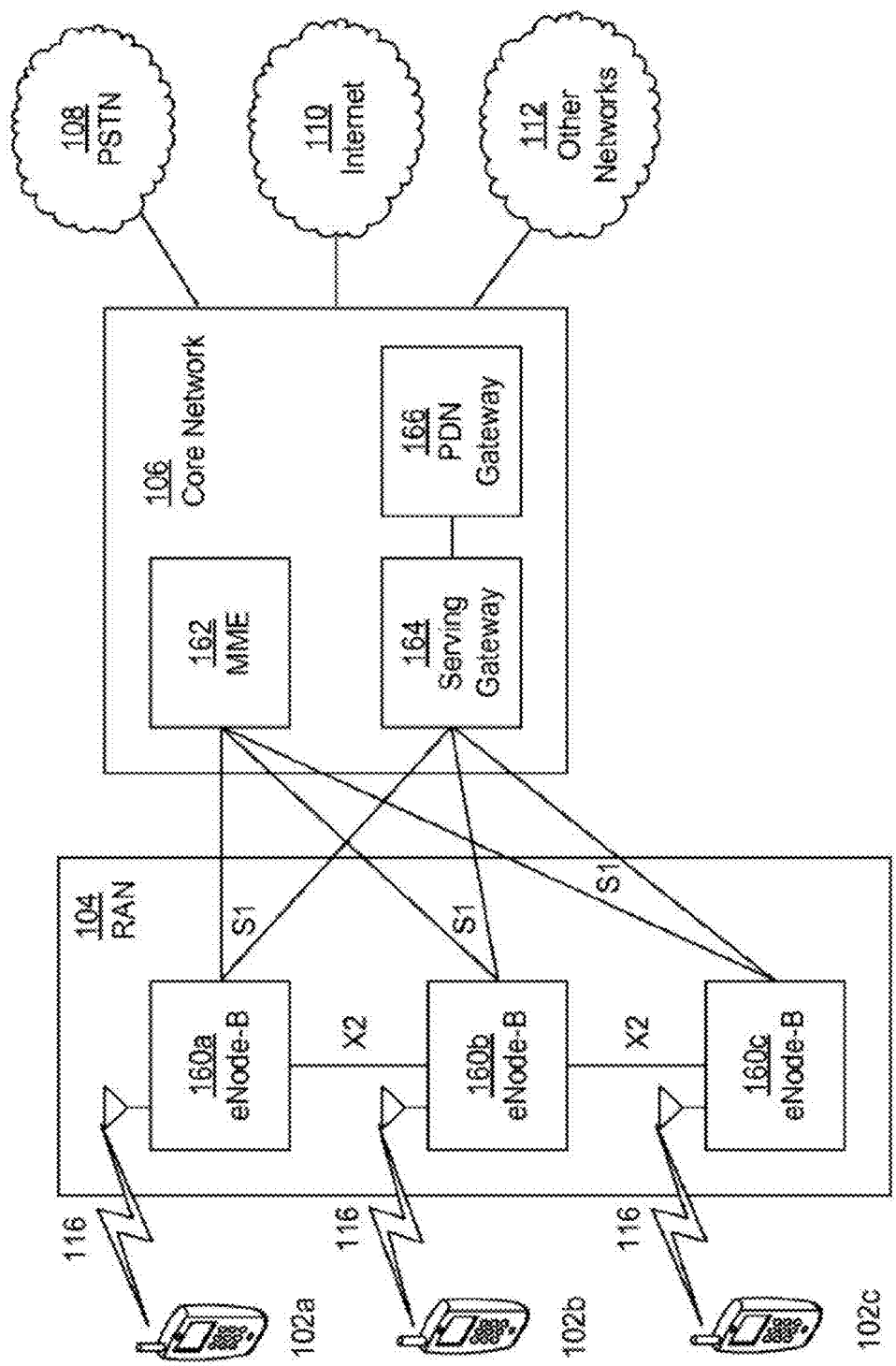
FIG. 1D is a system diagram of another example radio access network and an example core network that may be used within the communications system illustrated in FIG. 1A.

FIG. 1D is a system diagram of the RAN 104 and the core network 106 according to an embodiment. As noted above, the RAN 104 may employ an E-UTRA radio technology to communicate with the WTRUs 102a, 102b, 102c over the air interface 116. The RAN 104 may also be in communication with the core network 106.

The RAN 104 may include eNodeBs 160a, 160b, 160c, though it will be appreciated that the RAN 104 may include any number of eNodeBs while remaining consistent with an embodiment. The eNodeBs 160a, 160b, 160c may each include one or more transceivers for communicating with the WTRUs 102a, 102b, 102c over the air interface 116. In one embodiment, the eNodeBs 160a, 160b, 160c may implement MIMO technology. Thus, the eNodeB 160a, for example, may use multiple antennas to transmit wireless signals to, and receive wireless signals from, the WTRU 102a.

Each of the eNodeBs 160a, 160b, 160c may be associated with a particular cell (not shown) and may be configured to handle radio resource management decisions, handover decisions, scheduling of users in the uplink and/or downlink, and the like. As shown in FIG. 1D, the eNodeBs 160a, 160b, 160c may communicate with one another over an X2 interface.

The core network 106 shown in FIG. 1D may include a MME 162, a serving gateway 164, and a packet data network (PDN) gateway 166. While each of the foregoing elements are depicted as part of the core network 106, it will be appreciated that any one of these elements may be owned and/or operated by an entity other than the core network operator.

The MME 162 may be connected to each of the eNodeBs 160a, 160b, 160c in the RAN 104 via an S1 interface and may serve as a control node. For example, the MME 162 may be responsible for authenticating users of the WTRUs 102a, 102b, 102c, bearer activation/deactivation, selecting a particular serving gateway during an initial attach of the WTRUs 102a, 102b, 102c, and the like. The MME 142 may also provide a control plane function for switching between the RAN 104 and other RANs (not shown) that employ other radio technologies, such as GSM or WCDMA.

The serving gateway 164 may be connected to each of the eNodeBs 160a, 160b, 160c in the RAN 104 via the S1 interface. The serving gateway 164 may generally route and forward user data packets to/from the WTRUs 102a, 102b, 102c. The serving gateway 164 may also perform other functions, such as anchoring user planes during handovers between eNodeBs, triggering paging when downlink data is available for the WTRUs 102a, 102b, 102c, managing and storing contexts of the WTRUs 102a, 102b, 102c, and the like.

The serving gateway 164 may also be connected to the PDN gateway 166, which may provide the WTRUs 102a, 102b, 102c with access to packet switched networks, such as the Internet 110, to facilitate communications between the WTRUs 102a, 102b, 102c and IP enabled devices.

The core network 106 may facilitate communications with other networks. For example, the core network 106 may provide the WTRUs 102a, 102b, 102c with access to circuit switched networks, such as the PSTN 108, to facilitate communications between the WTRUs 102a, 102b, 102c and traditional land line communications devices. For example, the core network 106 may include, or may communicate with, an IP gateway (e.g., an IP multimedia subsystem (IMS) server) that serves as an interface between the core network 106 and the PSTN 108. In addition, the core network 106 may provide the WTRUs 102a, 102b, 102c with access to the networks 112, which may include other wired or wireless networks that are owned and/or operated by other service providers.

Figure 1E:
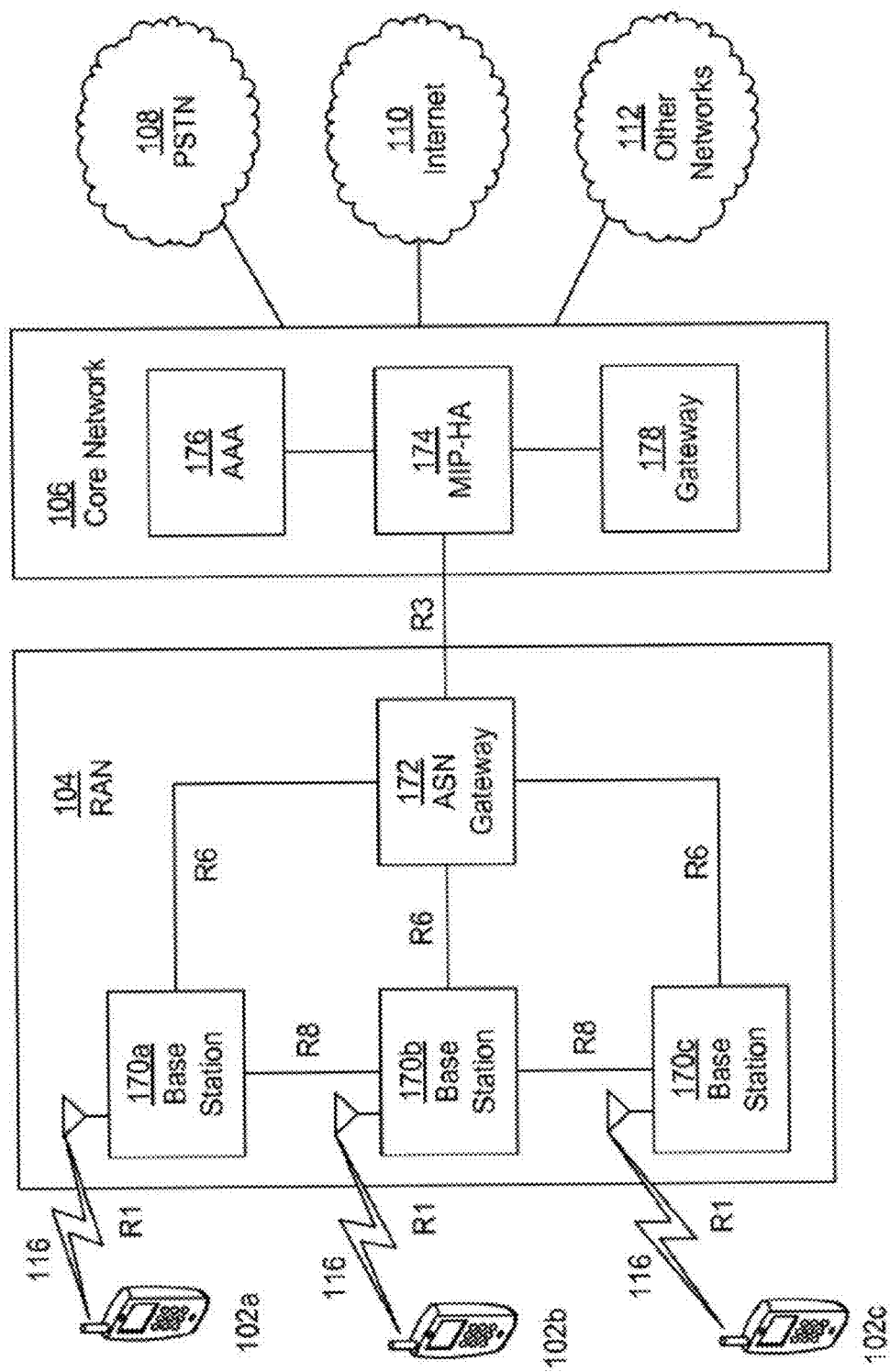
FIG. 1E is a system diagram of another example radio access network and an example core network that may be used within the communications system illustrated in FIG. 1A.
Figure 2:
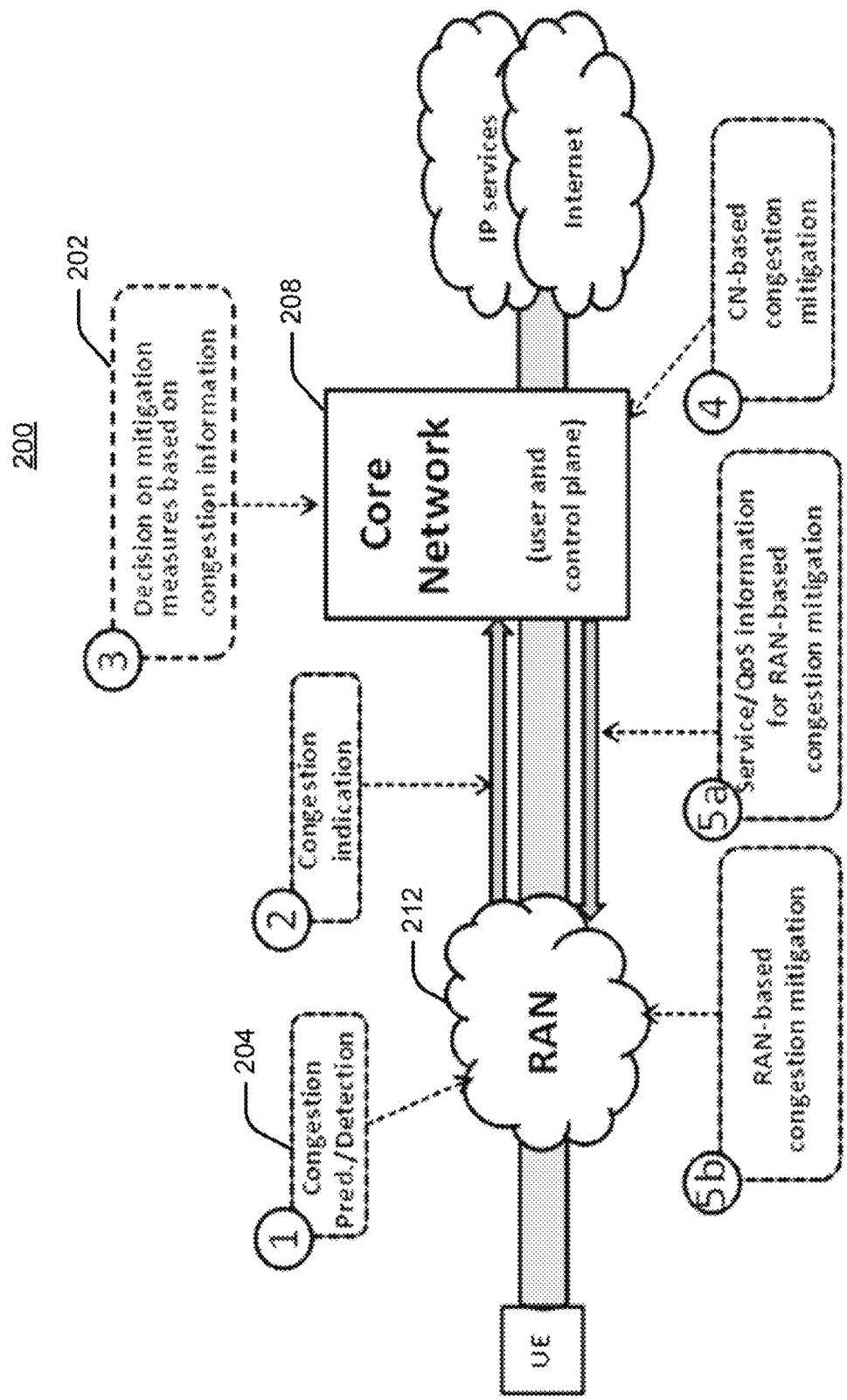
FIG. 2 is a system diagram of a possible embodiment of a system for user plane congestion management.

FIG. 1E is a system diagram of the RAN 104 and the core network 106 according to an embodiment. The RAN 104 may be an access service network (ASN) that employs IEEE 802.16 radio technology to communicate with the WTRUs 102a, 102b, 102c over the air interface 116. As will be further discussed below, the communication links between the different functional entities of the WTRUs 102a, 102b, 102c, the RAN 104, and the core network 106 may be defined as reference points.

As shown in FIG. 1E, the RAN 104 may include base stations 170a, 170b, 170c, and an ASN gateway 142, though it will be appreciated that the RAN 104 may include any number of base stations and ASN gateways while remaining consistent with an embodiment. The base stations 170a, 170b, 170c may each be associated with a particular cell (not shown) in the RAN 104 and may each include one or more transceivers for communicating with the WTRUs 102a, 102b, 102c over the air interface 116. In one embodiment, the base stations 170a, 170b, 170c may implement MIMO technology. Thus, the base station 170a, for example, may use multiple antennas to transmit wireless signals to, and receive wireless signals from, the WTRU 102a. The base stations 170a, 170b, 170c may also provide mobility management functions, such as handoff triggering, tunnel establishment, radio resource management, traffic classification, quality of service (QoS) policy enforcement, and the like. The ASN gateway 142 may serve as a traffic aggregation point and may be responsible for paging, caching of subscriber profiles, routing to the core network 106, and the like.

The air interface 116 between the WTRUs 102a, 102b, 102c and the RAN 104 may be defined as an R1 reference point that implements the IEEE 802.16 specification. In addition, each of the WTRUs 102a, 102b, 102c may establish a logical interface (not shown) with the core network 106. The logical interface between the WTRUs 102a, 102b, 102c and the core network 106 may be defined as an R2 reference point, which may be used for authentication, authorization, IP host configuration management, and/or mobility management.

The communication link between each of the base stations 170a, 170b, 170c may be defined as an R8 reference point that includes protocols for facilitating WTRU handovers and the transfer of data between base stations. The communication link between the base stations 170a, 170b, 170c and the ASN gateway 142 may be defined as an R6 reference point. The R6 reference point may include protocols for facilitating mobility management based on mobility events associated with each of the WTRUs 102a, 102b, 102c.

As shown in FIG. 1E, the RAN 104 may be connected to the core network 106. The communication link between the RAN 104 and the core network 106 may defined as an R3 reference point that includes protocols for facilitating data transfer and mobility management capabilities, for example. The core network 106 may include a mobile IP home agent (MIP-HA) 144, an authentication, authorization, accounting (AAA) server 146, and a gateway 148. While each of the foregoing elements are depicted as part of the core network 106, it will be appreciated that any one of these elements may be owned and/or operated by an entity other than the core network operator.

The MIP-HA 144 may be responsible for IP address management, and may enable the WTRUs 102a, 102b, 102c to roam between different ASNs and/or different core networks. The MIP-HA 144 may provide the WTRUs 102a, 102b, 102c with access to packet switched networks, such as the Internet 110, to facilitate communications between the WTRUs 102a, 102b, 102c and IP enabled devices. The AAA server 146 may be responsible for user authentication and for supporting user services. The gateway 148 may facilitate interworking with other networks. For example, the gateway 148 may provide the WTRUs 102a, 102b, 102c with access to circuit switched networks, such as the PSTN 108, to facilitate communications between the WTRUs 102a, 102b, 102c and traditional land line communications devices. In addition, the gateway 148 may provide the WTRUs 102a, 102b, 102c with access to the networks 11, which may include other wired or wireless networks that are owned and/or operated by other service providers.

Although not shown in FIG. 1E, it will be appreciated that the RAN 104 may be connected to other ASNs and the core network 106 may be connected to other core networks. The communication link between the RAN 104 the other ASNs may be defined as an R4 reference point, which may include protocols for coordinating the mobility of the WTRUs 102a, 102b, 102c between the RAN 104 and the other ASNs. The communication link between the core network 106 and the other core networks may be defined as an R5 reference, which may include protocols for facilitating interworking between home core networks and visited core networks.

ASAC information may be provided in order to permit ASAC operation for IDLE mode UEs. In order to make an ASAC feature work, the network may indicate to the UE which applications should stop accessing the network. A white and/or black list of applications may be preconfigured in the UE, or provided by the network. However, it may be difficult for both the network and the UE to identify a specific application in the white or black list. Because there may be thousands of applications, it may be difficult for the list to include all of the necessary application information. Therefore, it may be useful to efficiently and unambiguously define the applications to be barred, and convey this information to the UE.

One problem with the deactivation of ASAC used in congestion control mechanisms is that when the barring is deactivated, many of the previously barred UEs or applications may attempt to access the network again. Under these circumstances the accesses may be concentrated in a very short period of time. This could cause new congestion. Methods may be known in the art to disperse the accesses after the deactivation. However, since ASAC may have some unique characteristics, other methods for gradual and graceful deactivation of ASAC may be required.

Since there are different access control mechanisms in operation, any new ASAC control may need to interact with the known access control mechanisms. Furthermore, in a RAN sharing scenario, it may be possible for different operators to control different applications in the same RAN node. For example, if an eNB is shared by two operators (Operator A and Operator B), Operator A may want to prevent an application X from accessing the network. Operator B may want to perform access control on a different application Y. It may be necessary to support this type of operator specific access control, since different operators may have different application priorities already in effect in their networks. Also, congestion levels may be different for each operator sharing the RAN. Therefore, all of the operators may not want to apply ASAC at the same time for their users. Such scenarios may be taken into consideration and enabled.

Interaction with UPCON methods may be required. In ASAC it may be important to control which applications may access the network, and, similarly, in the case of UPCON, it may be important to control traffic generated from certain applications. A difference between the ASAC and UPCON requirements may be that, in the case of ASAC, access by the applications may be controlled at the time they start their network access. In UPCON, the applications may be controlled when they may already be generating traffic, and the network becomes congested. Furthermore, in UPCON a procedure may be provided wherein the RAN informs the CN policy and charging rules function (PCRF)/ANDSF of the congestion. In turn the ANDSF may provide a new policy to the UEs. However, a problem with this approach may be that when the RAN is already congested, the policy update itself may add to the traffic. Hence, a more efficient mechanism may be required which may be used frequently, and may be effective within a small duration of time with less signaling overhead.

Though ASAC may be targeted at IDLE UEs, there may also be similar requirements for preventing connected UEs from originating new services/applications. S1-131279, CR(0194) to 22.011 may reflect such a requirement. One difficulty in controlling connected UEs may be that the connection and the bearers may already be set up. It may not be possible to prevent a service/application layer from sending data over an existing connection/bearer.

With respect to ASAC for D2D communication, different rules may be needed by the network for direct D2D communication. This may be true because the D2D communication may be used to offload some of the network traffic, and the ASAC rules may therefore not apply to such data traffic or such applications. Also, the devices may need to check the ASAC rules before establishing a connection, or during an ongoing D2D connection. Such scenarios may be taken into consideration in order to properly manage application level access control.

Figure 3:
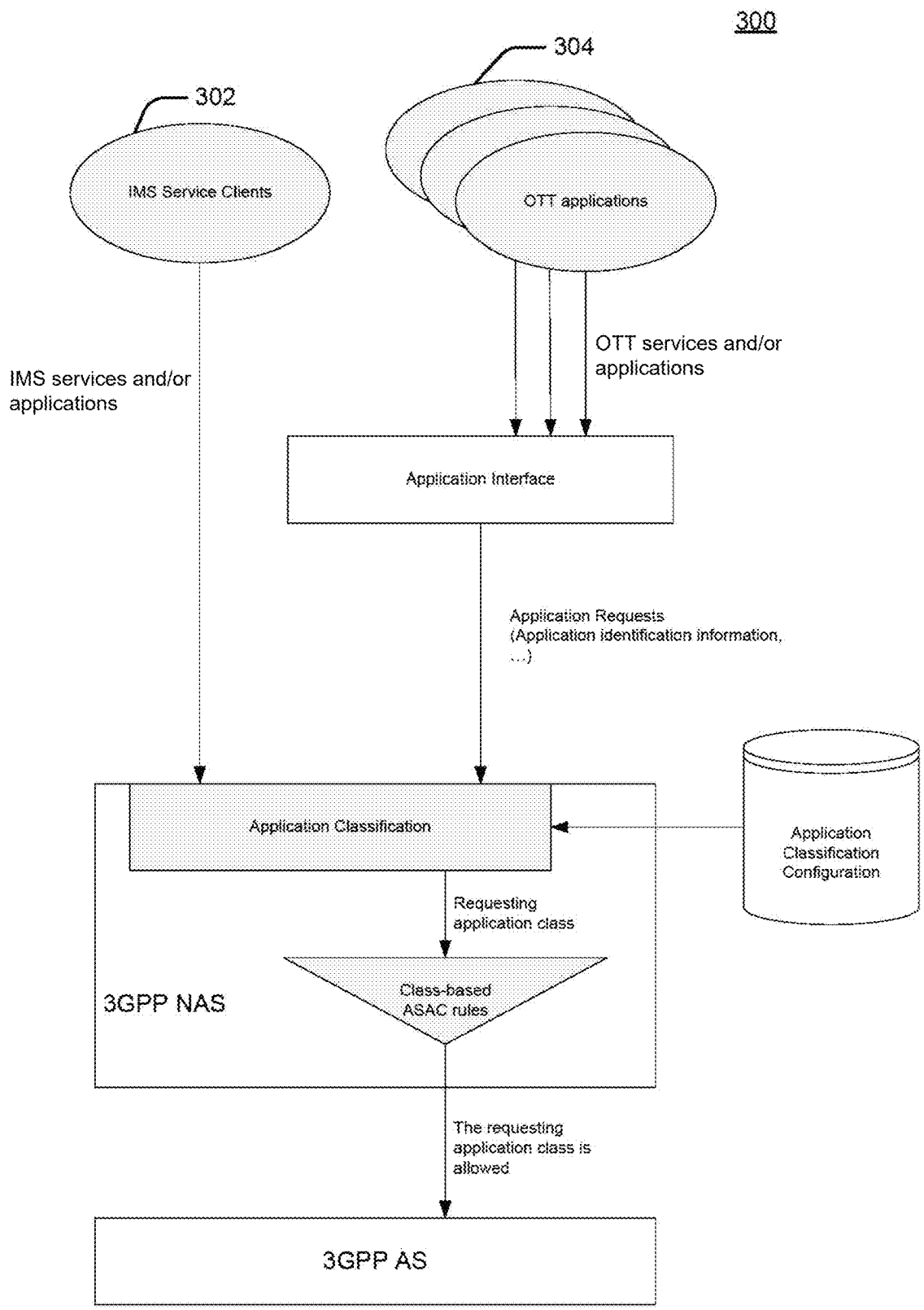
FIG. 3 is a UE model of a possible embodiment of a system for application class based control.

Referring now to FIG. 3, there is shown a possible embodiment of ASAC control system 300. In ASAC control system 300, ASAC control may be based on application classes rather than on individual applications. Such a system and method may include an application classification configuration, so that a UE may determine which class a requesting application may belong to. The application classification configuration may be located within a UE. The UE may compare the application class with the configured ASAC rules to decide whether the requesting application may be allowed.

It will be understood that a system and method, such as the system and method shown in control system 300, may apply to IDLE mode ASAC, connected mode ASAC, prevention of mobile originated communication (PMOC), etc.

The applications shown in ASAC control system 300, including the IMS services/applications of IMS service clients 302 and other over the top (OTT) services/applications 304, may be classified or categorized into application classes. The application classes may have different priorities with regard to ASAC control. Examples of the application classes may include emergency applications, high priority applications, medium priority applications, low priority applications, or any other types of applications operating within a network. For example, access for mobile terminated services may be considered as a special application class. Alternately, it may belong to one of the above application classes, e.g., a high priority application class.

In different situations, any other types of different classifications may be adopted. For example, in the case of disasters, two or more levels of classification may be enough: emergency applications and nonemergency applications. For other situations, any number of levels or more complicated classifications may be provided.

Furthermore, the classification information of applications may be preconfigured in UEs, or provided by the network through means such as ANDSF policies, open mobile alliance (OMA) device management (DM) objects, system information broadcasting, etc.

The application classification information may include, for example, a list of the application classes in an order of priority, or information indicating which applications may fall into which specific application classes. The application classification information may be identified in any number of ways, for example, by application identifiers. These ways of identifying application classification information may be used if the UE and network have a unified definition of application identifiers.

The application classification information may also be identified using a combination of application specific parameters. The application specific parameters may include an application name, an application provider name, an application server address, an application server port, an application protocol, or any other parameters.

Figure 4:
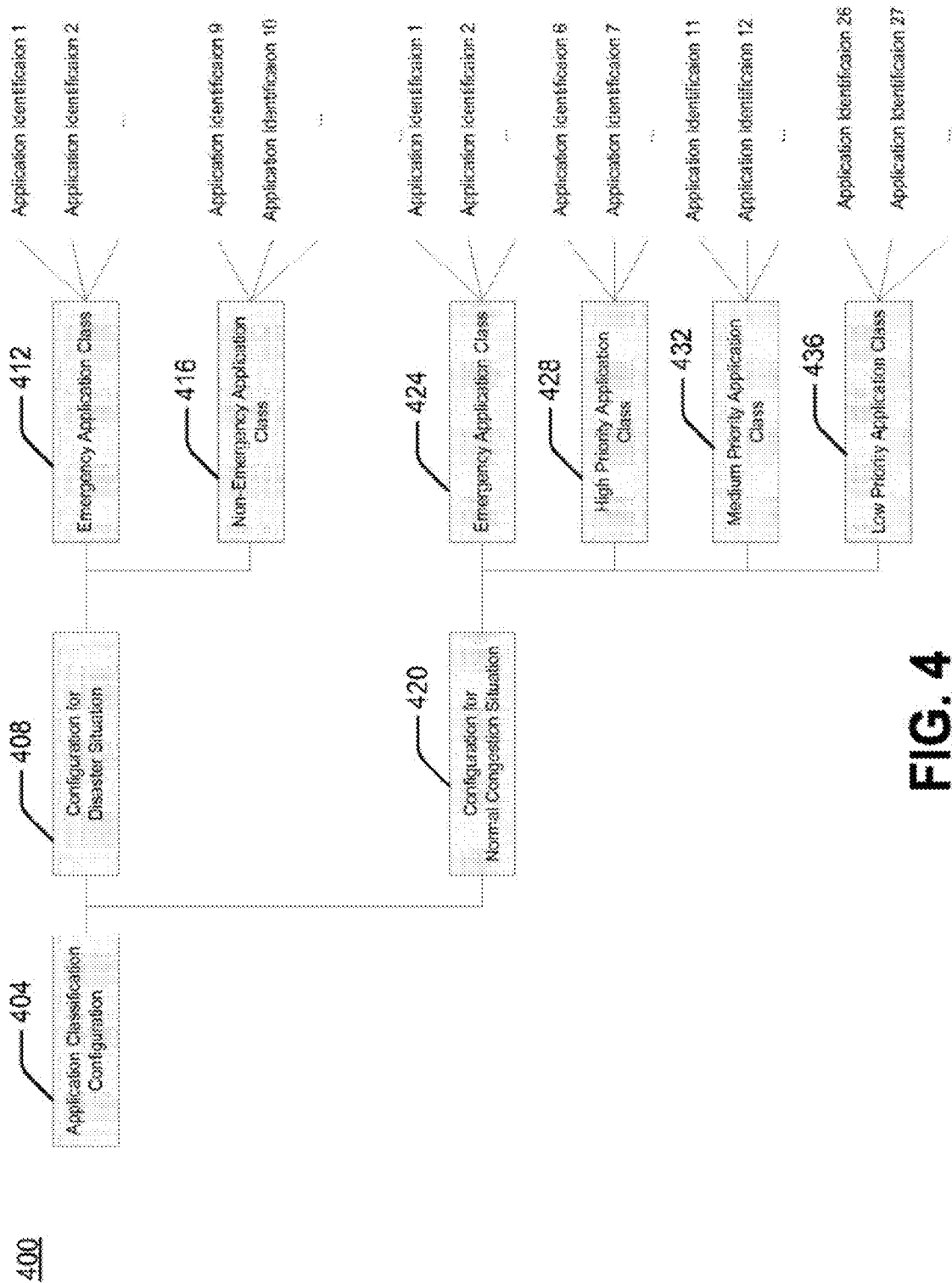
FIG. 4 is a block diagram of a possible embodiment of application classification information suitable for use in application class based control.

Referring now to FIG. 4, there is shown a possible embodiment of application classification information 400, which may be suitable for use in application class based access control. Some of the classification information in application classification information 400 may be configured in, or provided to, UEs. For MT services, an access may be categorized as a special MT application class if it may be configured as such. Additionally, an access may be categorized as one configured application class, e.g., a high priority application class or others. Furthermore, some application identification information may be available in a paging message. In this case, the information may be used to identify an application class similar to mobile originated (MO) applications. The application classification information 400 may also include an indication of the scenario to which an application classification configuration 404 may be related, if different classifications are provided for different scenarios. For example, application classification configuration 404 may include a disaster configuration 408 for disaster situations. The disaster configuration 408 may include configurations for emergency application class 412 and nonemergency application class 416. Another example of a configuration which may be included in application classification configuration 404 may be normal congestion configuration 420, for normal congestion situations. Normal congestion configuration 420 may include configurations for an emergency application class 424 and a high priority application class 428. Normal congestion configuration 420 may also include configurations for medium priority application class 432 and low priority application class 436. Application configuration 404 may have any number of additional configurations. Each of the application may have one or more application class identifications.

An application interface between an application and a 3GPP protocol stack may provide application classification information. For example, it may contain information application identifiers, a combination of application specific parameters, or any other relevant information. This may permit the 3GPP layer to determine which class a requesting application may fall into, and to thus apply application class based ASAC rules.

Since there may be many applications, it may be possible for application classification information 400 to be limited to application identifications for the applications that may be critical, well known or popular. Other applications that may not be identifiable in application classification information 400 may automatically fall into the lowest priority class.

Application classification information 400 may be provided by a home network operator. If a UE roams into a visited network, i.e. a network of another operator, the configuration may be considered invalid until it returns to its home network. Additionally, the UE may try to obtain a new configuration from a visited network (e.g., from a V-ANDSF or other visited network) if the visited network supports such a configuration.

Application classification information 400 may be provisioned explicitly, for example, by network entities such as ANDSF, DM, eNB, etc. Additionally, application class configurations may be provided, for example, in a UE by a self-training process.

When congestion problems caused by applications become severe, solutions that increase application awareness in the network may be sought, and application specific QoS control may be applied. Some solutions may extend current user plane packet headers, general packet radio service tunneling protocol user plane (GTP-U), or IP headers, to include indications of the application or flow priority. For example, the terms of service (ToS) or differentiated services code point (DSCP) field in the IP header may be used to indicate the application or flow priorities. These indications may actually be an equivalent of an application class.

If the priority indications are in the IP packets, the UE and its upper layers may receive the same indications which are determined by the network. By analyzing traffic metrics, such as source address, port, etc. and priority indications in the traffic, the UE may build a mapping relationship between specific application traffic and, for example, its priority application class. For example, if a UE sets up a TCP connection at port "xx" with a certain application server, and the downlink IP data over the TCP connection indicates priority "y," then the UE may build up the mapping between <server-addr, port xx> and priority "y," and store it in the UE. The next time the application tries to initiate a connection, the UE may identify the same priority/application class. The application may also check the application against an ASAC rule to determine whether the application class may be barred.

However, if a user plane packet priority indication is carried in a GTP-U packet header, the UE may not be able to utilize the information, since a GTP-U header may not be forwarded to the UEs.

The application class based ASAC rules for different possible scenarios may define a specific ASAC rule. An ASAC rule may include the identification of a rule, the situation where the rule may apply, (e.g., in a disaster or other situation), or the ACs that may be subject to the rule, e.g., AC0~AC9. Additionally, an application class based ASAC rule may define a white list of application classes, i.e., it may define applications belonging to the classes in a list that may be allowed. The ASAC rules may also define a black list of application classes, i.e., applications belonging to the classes in a list that may be banned. It may also define a period of time that the ASAC rule may remain activated if no explicit deactivation indication may be received, e.g., one hour.

Multiple rules may be defined for a scenario/situation according to different network congestion levels, for example severe, medium, mild, etc. Non scenario/situation specific rules (general rules) may also be defined, because the UE may not be aware of the scenario when ASAC needs to be activated in some cases.

Additionally, an ASAC rule may define, for example, whether an activation of the ASAC may be periodic, a time at which a rule of an ASAC in the UE may be activated, e.g., 9:30 am or 8:30 pm of a day, a time at which to deactivate an ASAC in the UE, or any other parameters related to the rule. This may be useful when the network congestion may be expected periodically, for example, during the busy hours of a day. Such ASAC rules may automatically trigger ASAC activation/deactivation without any indication from the network.

Furthermore, the location information of the UE may also be configured in an ASAC rule to automatically activate/deactivate a feature when the UE is in certain places/areas. The location information may be, for example, a cell ID, a closed subscriber group (CSG) ID, a GPS coordinate, or any other type of location information. For example, the ID of a cell that covers a metro station, where congestion may normally be observed, may be configured in an ASAC rule. Thus, when a UE enters the cell it may automatically activate the ASAC. In another example, a UE may deactivate an ASAC rule when it enters a closed or hybrid home evolved NodeB (HeNB) to which it may be a CSG member, if the network has triggered the activation. Alternately, the UE may ignore any ASAC activation indication from the network.

In a RAN shared by multiple operators, common ASAC rules may be configured for all operators/public land mobile networks (PLMNs). Alternately, operator or PLMN specific ASAC rules may be configured for each operator/PLMN. Even when operator/PLMN specific ASAC rules are defined, some ASAC rules, such as ASAC rules for emergency scenarios, or any other rules, may still be used by operators/PLMNs.

Similar ASAC rules may be applied to both MO and MT accesses. Alternatively different MO specific and MT specific ASAC rules may be defined. For example, in some scenarios, a network may allow only emergency applications for MO, and both emergency and high priority applications for MT.

In a manner that may be similar to an embodiment of application classification information 400, the ASAC rules may be preconfigured in the UE, or provided by the ANDSF policies, OMA DM objects or eNB system information broadcasting. If necessary, UE specific ASAC rules may be provided through dedicated NAS or radio resource control (RRC) signaling.

It may be noted that a design of ASAC rules, with the possible exception of the application class based black/white lists, or others, may also apply to other non application class based ASAC rules. Triggering of ASAC activation/deactivation in the UE may be performed by configuring time or location based criteria in the UE. When these criteria are met, the ASAC may be automatically activated or deactivated.

More generally, activation and deactivation may be triggered by the presence/non presence of ASAC related information (e.g., ASAC rules). This may be especially true when ASAC related information may be provided by system information broadcasting, similar to ACB or EAB feature. An additional activation/deactivation indication from the network may be an indication that ASAC related information may be provided in advance, e.g., through ANDSF, OMA DM, a SIB or dedicated RRC signaling. This may occur when an indication from the network to activate/deactivate a feature may be available, and the feature may be activated or deactivated in the UE. The indication may be in any form. For example, the indication may be a bit/bits in the master information block (MIB), SIBs, an IE in the paging message, an ANDSF policy push, etc.

Thus, when a UE receives, for example, earthquake tsunami warning system (ETWS) paging, or another disaster situation indication, it may automatically activate the ASAC if general or disaster scenario specific rules may be available. Moreover, an explicit ASAC activation indication may be carried in a paging message such as an ETWS paging message.

Additionally, some indications of a network congestion situation, such as a presence of SIBs for ACB, or EAB, or SSAC, or others, may automatically activate the ASAC if the rules may be available in the UE. Even if the UE or applications may not be subjected to ACB, EAB or S SAC, an ASAC may be activated.

If an operator/PLMN specific ASAC rule may be configured for a shared RAN, a common activation or deactivation indicator may be provided for UEs belonging to different operators/PLMNs. The indicator may be provided to activate/deactivate a feature with common or different ASAC rules. Alternatively, an operator/PLMN specific activation/deactivation indication may be provided by the network. In this case, a UE belonging to the specific operator/PLMN may activate/deactivate the feature, and other UEs may not be affected. This may be especially useful when the RAN is shared, and each participating operator may only use a percentage of the RAN resources. Under these conditions some operators may reach their quotas and need to activate ASAC, while other operators may not.

The network may update the ASAC rules in order to gradually allow additional applications to access the network as the network congestion situation improves, before the network explicitly deactivates the ASAC. For example, when the network congestion may be very severe, a network provided ASAC rule may allow only emergency applications to access the network. When the network congestion is mitigated, the network may update the rule to also allow higher priority applications to access the network. Using this method, or other methods, the deactivation process may be gradual and graceful, and concentrated access may be avoided.

Figure 5:
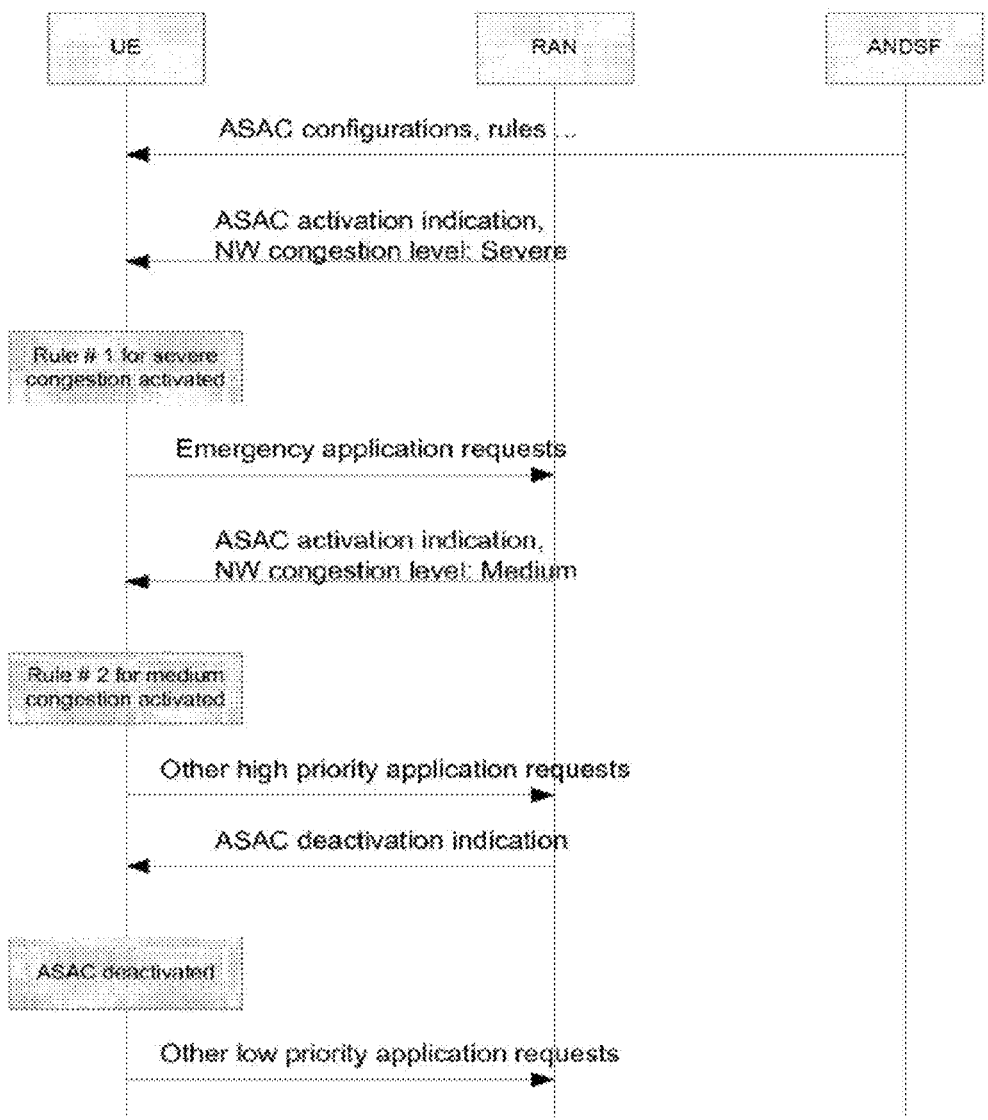
FIG. 5 is a process flow of a possible embodiment of a procedure for indicating congestion levels and updating rules.

Referring now to FIG. 5, there is shown a possible embodiment of procedure 500 for indicating congestion levels and updating rules. For some dynamically provided ASAC rules, e.g., SIB broadcasted ASAC rules, or others, it may be easy for the network to directly update the rules. For statically preconfigured, or semistatically provided ASAC rules, e.g., rules provided by the ANDSF or OMA DM, or others, the network may indicate different congestion levels to activate different ASAC rules in the UE.

As previously described, ASAC rules may define the ACs to which they apply. Thus, the network may also adjust the number of ACs in the active ASAC rules according to different congestion levels, and thereby achieve a gradual and graceful deactivation procedure.

In the case of ASAC for MT traffic in an IDLE mode, an MT application ID may be signaled in page or MT specific ASAC rules. This may assume that the MME does not have application awareness. It may also assume that the ASAC priority may be directly derived from the QoS parameters of an evolved packet system (EPS) bearer transporting the application packet. A downlink (DL) notification message may be extended to include an application ID for the packet buffered at a serving gateway (SGW). The MME may include this information in an S1 page message. An eNB may transmit page messages with an application ID.

Some ASAC rules may be specifically defined for MT access. For example, different black lists may be defined for MO and MT. In some nonemergency scenarios, a UE may bypass ASAC for MT. In emergency ASAC conditions, MT access may be subject to ASAC barring.

In DL notification/paging filtered at the MME or eNB, the subscription profile downloaded from a home subscriber server (HSS) to an MME may provide the allowed App-ID/QCI/allocation and retention priority (ARP)/functional programming interface (FPI) per load condition. Using a standard defined or implementation specific interface, the MME may acquire a RAN load condition. The MME may thus acquire the two pieces of information, along with other information, in order to determine whether to perform a page to a specific eNB for a specific UE.

Furthermore, the page may be filtered by an eNB according to paging priority, possibly because the load information may be unknown to the MME. The MME may be able to perform filtering based on UE subscription, application ID, sub-quality control index (QCI), flow priority indicator, ARP, QCI, or other information in order to derive a paging priority. The paging priority may be consistent with an application priority configured by ASAC DM/ANDSF for a particular UE. If a visited public land mobile network (VPLMN) ASAC policy is observed when roaming, inter-operator agreement may be needed, such that a QoS/application parameter in home public land mobile network (HPLMN) may be mapped to a policy/priority configured by the VPLMN.

A DL notification message may be extended to include an application ID, sub-QCI or flow priority indicator for a packet buffered at a SGW. The MME may be based on the EPS bearer ID, QCI, ARP, and/or sub-QCI/flow priority indicator/application ID, to determine a paging priority. The eNB may inform the MME of the RAN congestion information (e.g., no page for paging priority below certain level). The MME may use the paging priority and the RAN congestion in order to determine whether to page a UE. Alternatively, an S1 page may be sent to the eNB, and the eNB may decide whether to perform a page based on paging priority. If an S1 page may be sent, the MME may decide not to perform a repage based on the RAN/eNB congestion information. The UE may be required to perform MT access by ignoring ASAC parameters/configurations.

The MME may send a suspend notification, or a DL data notification acknowledge, to inform the SGW to suspend a particular EPS bearer, or to suspend the DL notification of a downlink packet of a particular sub-QCI/flow priority/application ID. Such packets may be dropped by the SGW. In addition, the SGW may inform the PGW of the suspension of a particular bearer, instead of the entire PDN connection. Thus, there may be information regarding selective suspension of data transmitted from the MME to the SGW.

There may be interaction between ASAC and other congestion control mechanisms. For example, in some LTE systems, several congestion control mechanisms, such as ACB, SSAC and EAB, may be defined. ASAC and SSAC may serve similar purposes, and ASAC may be more advanced and may have finer granularity of target services/applications. Thus, it may be unlikely that a network would activate both SSAC and ASAC at the same time. However it may be possible for the network to activate both ACB and ASAC, or both EAB and ASAC, or even ACB/EAB/ASAC at the same time.

If ACB (or EAB) and ASAC are both activated, and the UE is subjected to both, the ASAC may be checked before the ACB (or EAB). This may be preferable, since an ASAC check may be performed in the NAS while the ACB (or EAB) check is done in the AS, and the NAS may not be aware of whether ACB may be activated. If an application passes an ASAC check, but the UE's AC fails the ACB (or EAB) filter, access to the network may not be allowed. However, if an application passes ASAC, and the application class is, for example, emergency, the NAS layer may indicate to the AS and the ACB (or EAB) that the check may be bypassed.

It may also be possible for only one check to be carried out, and other checks may be ignored. For example, when EAB and ASAC are both activated in the network, some UEs may only be subjected to an ASAC check, but not an EAB check. Some UEs may be subjected to both. For the latter case, only an EAB check may be performed and the ASAC check may be ignored.

The ASAC may be located in a RAN shared by multiple operators. In a RAN shared by multiple operators, commonly defined ASAC rules may be configured on a PLMN specific or on an operator specific basis. The ASAC rules may be associated with a particular operator, e.g., each rule may have an extra parameter indicating the PLMN ID of the operator to which the rule may apply. This may be in addition to the parameters listed above. Furthermore, the SIB information broadcasted in a shared RAN may indicate whether a particular operator is applying ASAC. This may be achieved using an ASAC flag for each operator in the SIB information. If the flag is active, the UE may act according to the ASAC rules, and control certain applications for access to the network. Otherwise, the UE may behave normally. In certain situations the RAN owner of a shared RAN, i.e., an operator who may allow other operators to use an eNB, may want to control certain applications for all PLMNs for a particular reason. For example, an application may cause an undue load on the whole RAN node. In this situation, the RAN owner may request the hosted operators, e.g., operators sharing the RAN, to change their ASAC policy for the UEs, and to include the particular application or class of applications in the black list. The hosted operators may then comply with the request of the RAN operator and include the application in the ASAC list.

Alternatively, the RAN operator may indicate, for example, in one of the SIBs that its ASAC policy may be global, i.e., the ASAC policy may apply to all UEs from all of the operators/PLMNs sharing the RAN.

In a commercial network RAN, it may be known that, for example, congestion may occur every 700-800 seconds, and may last for 1-2 seconds. Hence an efficient mechanism which may be effective within small durations of time, with less signaling overhead, may be used.

In accordance with a user subscription, the ANDSF may provide multiple policies to the UEs. Each policy may have an index. Each policy may contain a list of allowed (or alternatively not allowed) applications. The multiple policies may be provided to the UE before there is congestion, while the network load may still be manageable. When a RAN becomes congested, and it informs the CN (PCRF/ANDSF), the ANDSF may select one of the policies for a user. The selection may be based on a user subscription. The ANDSF may signal the index of the selected policy to the UE. Since signaling an index may be sufficient when the RAN is congested, it may add less signaling overhead at run time. Furthermore, previously provided multiple policies may be reused once or repeatedly by signaling the appropriate index based on situations such as the severity level of the congestion. The ANDSF may signal indexes to different UEs in a synchronized manner so that congestion may be controlled gradually and gracefully.

When the RAN reports to the CN that the congestion may be over, the ANDSF may send an original index to a UE. This may also be synchronized in such a way that different traffic generated from the allowed applications in different UEs may be gradually and gracefully ramped up. In ANDSF there may be only one validity timer. However, it may be possible to have a separate validity timer for each policy. Upon expiry of a timer, the UE may delete the policy and alternatively inform the ANDSF. The UE may update the indexes of the remaining policies. It may also be possible that upon expiry of a timer the UE may mark the policy for deletion and inform the ANDSF. After receiving a command from the ANDSF the UE may delete the policy and update the indexes. At any time, the ANDSF may add an additional policy, which may have been provided earlier to the UE, to an existing policy list. The ANDSF may signal this to the UE by setting a new policy indicator, or the index of the new policy along with the content of the policy. When the UE receives the new policy indicator, it may add the received policy to its list and update the indexes accordingly.

Similarly, the ANDSF may delete a policy from a previously provided list by sending the index of the policy to the UE. The ANDSF may indicate that the index should be deleted using a flag. When the UE receives this message it may delete the policy and update the indexes. Alternatively, in a case of both addition and deletion of policies from the list, the UE may confirm the execution of the command with the ANDSF. It may also be possible for the ANDSF to partially update an existing policy. This may be done by indicating an index of the policy. A flag indicating a partial update may be provided. Upon reception of the partial update message the UE may update a selected policy by modifying the indicated partial content. Alternatively, multiple policies and updates such as the above may be performed by OMA DM.

In another embodiment, in order to speed operations, it may be possible for the RAN to not inform the CN (PCRF/ANDSF) about the RAN congestion. Rather, the RAN may signal indexes directly to the UEs. In this method multiple policies may already be provisioned in the UE by ANDSF/OMA DM.

In yet another embodiment, the RAN itself may provide a list of multiple policies to different UEs. This may be done, for example, at the RRC. The policy list may be different for different UEs depending upon their subscription levels. The RAN may have access to the subscription level of the UE at the time of a connection setup. When there may be congestion in the RAN, the RAN may indicate an index of a policy for a UE to follow. The RAN may indicate the index by signaling the appropriate index based on a situation, such as a severity level of congestion, or other situation. The RAN may signal indexes to different UEs in a synchronized manner, so that the congestion may be controlled gradually and gracefully. When the RAN detects that congestion is over, it may choose to send the original index to the UE. This action may also be synchronized in such a way that different traffic generated from the now allowed applications in different UEs may be gradually and gracefully ramped up.

A validity timer for the policy list may be introduced. The validity timer may be a single timer for a complete list. It may also be a separate timer for each policy in the list or portion of the list. Upon expiry of the timer the UE may delete the policy and alternatively inform the RAN. It may also update the indexes of the remaining policies. It may also be possible that upon expiry of the timer the UE may mark the policy for deletion. The UE may inform the RAN. After receiving a command from the RAN, the UE may delete the policy and update the indexes.

At any time the RAN may add an additional policy to an existing policy list, wherein the existing policy list may have been provided to the UE earlier. The RAN may signal this to the UE by setting a new policy indicator, or an index of the new policy, along with the content of the policy. When the UE receives the new policy indicator, it may add the received policy to the list and update the indexes accordingly. Similarly, the RAN may delete a policy from the previously provided list by sending the index of the policy, and indicating by a flag that the index may be deleted. When the UE receives this message it may delete the policy and update the indexes. In a case of both addition and deletion of policies from the list, the UE may confirm execution of the command with the ANDSF.

It may also be possible for the RAN to update an existing policy only partially. This may be done by indicating an index of the policy. A flag indicating a partial update may be provided. Upon reception of this message the UE may update the selected policy by modifying the indicated partial content.

In another embodiment, when the UE is informed by the network (eNB/ANDSF/DM, etc.) which indexed policy to follow, the UE may continue using the received policy as long as a new index is not received. Alternatively, the UE may follow the indicated policy for a configured duration of time. After expiry of the configured time, the UE may check with the network to determine which policy may be followed. Additionally, the UE may revert to a default policy. A default policy may be one of the policies in a multipolicy list. The default policy may be indicated explicitly by means of a flag. Alternately, the default policy may be indicated implicitly by means of a predefined index, e.g., it may be the first policy in the list. When a new policy is added, the UE may be informed which policy to follow. If there is no explicit indication, the UE may continue using an old policy for a configured time interval. To avoid ping pong, a hysteresis mechanism may be added. In a hysteresis mechanism the UE may discard a new message received in a time window, if two consecutive messages (containing different policy indexes) are received from the network within a certain configured time interval. The time window may start from the reception of a message containing a different index. Or, for example, it may be reset every time a new message may be received.

Mechanisms such as, e.g.: (i) providing multiple policies preconfigured at the UE containing different application lists (allowed/or not allowed), and (ii) indicating the current index based on a situation, may be applicable to both UPCON and ASAC.

In a further embodiment the RAN may inform the CN of congestion and indicate the direction of the congestion, i.e., UL congestion, DL congestion or both UL and DL congestion.

In another embodiment for UPCON, it may be possible to add a list of allowed (or alternatively not allowed) applications to the TFT. Multiple TFTs per bearer may be provided to the UE beforehand. At any time the UE may follow one of the TFTs of a bearer. The TFT may be a default TFT for the bearer. Alternately, it may follow any other index in the TFT list for the bearer which may be provided by the network dynamically, depending upon congestion or any other factors. A default TFT for a bearer may be one of the TFTs in a multi TFT list. The default TFT may be indicated explicitly by means of a flag. Alternately, it may be indicated implicitly by means of a predefined index (e.g., the first TFT in the list). The RAN may indicate the congestion to the PCRF, possibly with the severity of congestion at a RAN, and/or the direction of congestion. The direction of the congestion may include UL, DL or both, based on a severity level. The PCRF may indicate this to the PGW. The PGW may send an indication to the UE related to the TFT index to be used.

If only the DL is congested, the PGW may not send any TFT index change to the UE. The PGW may not send any TFT index change if the PGW has recently changed the TFT index that it is using for the DL. If the UL or both directions is congested, the PGW may choose to send a TFT index to be used to the UE. Based on the TFT index, and the application list inside the TFT index, the UE may filter traffic from the mentioned applications. It may either allow traffic only from those applications, or it may not allow traffic only from those applications. The procedures mentioned herein that are related to updating/addition/deletion of policies may thus provide a multi policy list. The multi policy list may be applicable for updating/addition/deletion of the TFT in the TFT list for a bearer. It may also be possible that a multiple applications list may be added in one TFT. Instead of indicating the TFT index of an application, the list may be indicated. This may depend on the congestion and/or the severity and/or the direction of the congestion. Similarly, it may be done with the service data flows (SDF).

Any type of statistics may be collected for ASAC and UPCON. The statistics may be collected whenever an eNB, or any other type of node, requires additional information. The statistics may be collected periodically, based on other events, or at any other time.

Additionally, the UE may provide further information to the network. The further information from the UE may include, for example, statistics regarding running applications. For example, the statistics may include how much data the applications have exchanged (in UL/DL) in a certain time window. It may also include the predicted UL/DL data per application in a future time window. The information from the UE may also include a total data exchange predicted, a level of activity in the past/future, a time when further activity may be expected, threshold based information, or any other parameters, e.g., the type, content, etc. of information.

A UE may provide this information in a NAS message to the MME. The MME may insert the information into the eNB's UE context. Or, it may send the information to the PCRF or the ANDSF. The UE may also provide the information directly to the eNB in a RRC message.

Based on this information, the network may be better able to target a selected UE and/or a selected application in a UE. This may better ease congestion by means of ASAC and/or UPCON mechanisms.

The eNB or other node (PCRF/ANDSF) may update policy (or a new message for controlling a targeted UE or a targeted application in a UE) based on the information selectively targeting the UE and applications.

Deep packet inspection (e.g., traffic detection function (TDF) or others) in the network may determine the top few applications consuming most of the resources in the network. A top few applications list may be configured in various UEs by means of ANDSF/OMA DM/eNB RRC, etc. Each application may have a specific index. The network may command a UE to provide statistics if the UE has any running application in the list. The UE may respond with statistics determined from corresponding applications, along with index of the application from the configured application list.

PMOC for a Connected Mode UE

To prevent a connected mode UE from launching a new application, a method such as the following and others may be used. These methods may work for those applications that may be identified by packet filters.

Mobile Origination Prevention Through UL-TFT Packet Filters

A new attribute having an allow attribute or a block attribute may be added to the TFT packet filter attributes. Using packet filters having an allow/block attribute, an application may be permitted access in a communication system, and the application traffic may continue, if the new attribute indicates allow. Otherwise, if the new attribute indicates block, the application may be barred from access to the communication system, and the application traffic may be blocked.

Figure 6:
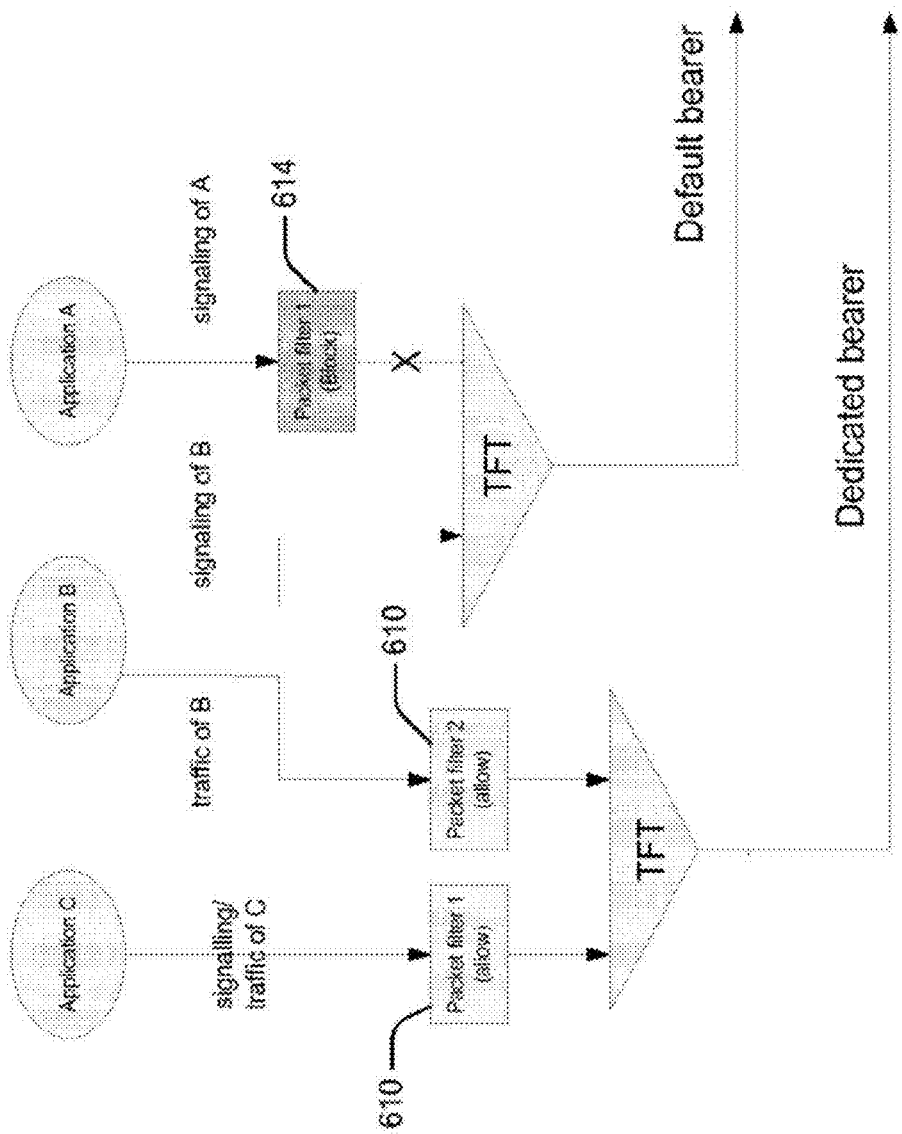
FIG. 6 is a block diagram of a possible embodiment of packet filters having an allow/block attribute.

Referring now to FIG. 6, there is shown a TFT packet filter system 600. In TFT packet filter system 600, an allow attribute may be provided for TFT packet filters, such as allow TFT packet filters 610. Additionally, a block attribute may be provided for TFT packet filters, such as block TFT packet filter 614. The TFT packet filter system 600 may also have a black list of the applications that it will not allow the connected UEs to initiate. Thus, block TFT packet filter 614 may be explicitly configured with the new attribute block in order to block the applications, and notify the default bearer or the dedicated bearers.

For example, application signaling traffic (such as session initiation protocol (SIP)) may normally be mapped to the default bearer, if there are no related TFTs defined for it. If an explicit TFT packet filter 614 is created (with the new attribute block) for the application, and the TFT for the default bearer is installed, the application signaling may be trapped by the TFT packet filter 614, and the application may not pass through.

The system may configure such allow/block filters during an attach procedure or a service request procedure, or the system may initiate a bearer modification procedure to update the UL-TFT.

If a black list of applications is long, it may not be practical to install enough packet filters with the block attribute in the UE. A more practical way may be to install only the packet filters corresponding to the allowed applications. Furthermore, it may not be practical to prevent other traffic that does not have a matching filter from going to the default bearer.

A method may be implemented to prevent traffic from going to a default bearer if a matching filter is not found. An explicit indication may be sent to the UE to indicate that any traffic that does not have a matching filter may be dropped. Thus, such traffic may not go to the default bearer. This indication may be carried in several EPS session management (ESM) messages, such as activate default/dedicated EPS bearer, modify EPS bearer request, etc.

Additionally, an indication bit may be added in the TFT format (e.g., using the reserved bits of "TFT Operation Code") to indicate that the traffic should be dropped if a matching filter is not found in the configured filters in the TFT. A TFT may be installed for the default bearer. The TFT may include the packet filters for allowed applications (in addition those already allowed by the dedicated bearer TFTs) and the special indication. Furthermore, a wild card packet filter with a block attribute may be configured in the TFT of the default bearer. Any traffic that does not find a matching filter may be matched to the wild card filter and blocked.

WiFi offloading may occur. The result of an ASAC check in the UE may be used as a trigger to start the WiFi offloading. If an application fails an ASAC check and a WiFi connection is available, the UE may continue to send the application signaling/data over the WiFi connection. If an application fails an ASAC check, and a WiFi connection is not available at the time, the UE may start scanning and associating with WiFi network.

ASAC and mobility procedures may be provided. The result of an ASAC check in the UE may also be used as a trigger to start processes such as intra/inter frequency or inter RAT mobility procedures. If an application is barred due to ASAC, the UE may try to start reselecting another suitable intra/inter frequency or inter RAT cell that may not be congested. This may occur even if the $S_{rxlev}$ and $S_{qual}$ of a current cell may not fulfill the criteria to initiate cell reselection measurement.

The cell ranking criteria for reselecting a new cell may be relaxed if the reselection is due to ASAC barring. For example, the ranking of a target cell may not be better than the serving cell. As long as the $S_{rxlev}$ and $S_{qual}$ of the target cell are better than a minimum threshold, the UE may be allowed to reselect the target cell.

ASAC may also be applied to D2D communication. There may be applications which may be controlled by ASAC rules, but some or all of the applications may be allowed by the network, if the application data is sent over a D2D communication link instead of the network. Therefore, a separate policy or rule may be added to the ASAC indicating whether the application is allowed/disallowed to access the network in different cases, e.g., core network communication, D2D communication, or both.

Establishment of D2D communication may be due to a particular application on a device requesting a D2D connection. If the particular application is controlled by ASAC rules, the D2D may check the ASAC rules to determine whether access for the application may be allowed before establishing the D2D connection. When a first UE sends a request for D2D radio bearer establishment/PDN establishment, it may check which application requested the connection establishment before sending the request. This may be performed by querying for the application ID in the NAS layer as described herein. If the particular application is not controlled by ASAC rules, the D2D connection request may be sent to a second UE. The same procedure may be performed by the second UE to determine whether the application may be allowed before accepting the request for connection establishment. If the ASAC rules allow the application, the request may be accepted. Alternately, if the application is controlled by ASAC rules, the request may be rejected with an indication that it is rejected because of ASAC.

Furthermore, while an ongoing D2D is taking place, it may be possible for the network to include an application on the D2D link, for a reason such as radio congestion on the D2D link or an emergency. If the ongoing D2D communication is established for a particular application, and the ASAC is activated, the link may be torn down immediately. Alternately, the D2D connection may be suspended until a time when the application access is allowed again by ASAC rules. (The D2D context of at least one of the UEs may be maintained by the eNB during the suspension.) A suspension of the D2D link may avoid the signaling required for reestablishment of the D2D communication link.

At least one AC identifier may be provided for indicating an AC that may be subject to the rule. A communication network may update the rule. The communication network may update the rule according to a level of congestion in the communication network. The communication network may update the rule to gradually permit access by the applications of the plurality of applications. Respective priorities may be provided for the rules of the plurality of rules. A respective rule of the plurality of rules may be determined according to a congestion level of the plurality of congestion levels. Access may be permitted or barred during an IDLE mode of the UE. Access may be permitted or barred during a connect mode of the UE. Respective priorities may be provided for the application classes of the plurality of application classes. The respective priorities may include emergency priority, nonemergency priority, high priority, medium priority or low priority. The application class may include application classification information. The application classification information may include at least one application specific parameter. The application classification information may include at least one application identifier. The application classification information may include an order of priority. The UE may determine that the application has caused a page for applying the rule to MT traffic.

An MT traffic specific rule may be configured. The MT traffic specific rule includes an application ID. The page includes the application ID. An eNB transmits the page and the application ID. The rule is applied to the MT traffic according to a determination that the application class applies to the page. The page is filtered by an MME. The page is filtered by the MME according to an application ID. The page is filtered by the MME according to a UE subscription. The page is filtered by an eNB. The page is filtered by the eNB according to a paging priority. A barred application is blocked. The rule is associated with an operator of the plurality of operators. The plurality of operators includes a host operator and a hosted operator. The host operator requests the hosted operator to update the rule. The rule is provided with an index. The rule is selected according to the index. A CN selects the rule according to the index. The CN selects the rule according to a level of congestion. An ANDSF selects the rule according to the index. Access is permitted or barred according to location information of the UE.

The location information is a cell identification. The location information is a GPS coordinate. A filter is provided for filtering communication network traffic. A packet filter is provided for filtering communication network traffic. A TFT is provided for filtering communication network traffic. The filter includes a filter attribute. The filter attribute includes an allow attribute for permitting access. The filter attribute includes a block attribute for barring access.

Thus, access in a communication network is permitted or barred according to a determined application class. The application is classified into the determined application class. A home network classifies the application into the application class. A 3GPP layer classifies the application into the application class. A visited network classifies the application into a further application class. A UE has a preconfigured application class. Access is permitted or barred according to a comparison of the determined application class with a rule.

The rule includes a list of applications. Access by the applications of the list of applications is permitted or barred according to the comparison of the determined application class with the rule. A period of time the rule is active is provided. A time at which the rule becomes active is provided. The rule is determined according to a level of congestion of a communication network.

The level of congestion is determined according to a SIB. The rule includes at least one AC identifier for indicating an AC that is subject to the rule. A communication network updates the rule. The communication network updates the rule according to a level of congestion in the communication network.

The communication network updates the rule to gradually permit access by a plurality of applications. There is a plurality of rules. Respective priorities are provided for the rules of the plurality of rules. There is a plurality of congestion levels. A respective rule of the plurality of rules is determined according to a congestion level of the plurality of congestion levels.

Access is permitted or barred during an idle mode of the UE. Access is permitted or barred during a connected mode of the UE. Respective priorities are provided for the application classes of a plurality of application classes. The respective priorities include emergency priority, nonemergency priority, high priority, medium priority or low priority. The application class includes application classification information. The application classification information includes at least one application specific parameter. The application classification information includes at least one application identifier. The application classification information includes an order of priority.

The UE determines that the application has caused a page for applying the rule to MT traffic. An MT traffic specific rule is configured. The MT traffic specific rule includes an application ID. The page further includes the application ID. An eNB transmits a page and the application ID. The rule is applied to the MT traffic according to a determination that the application class applies to the page.

The page is filtered by an MME. The page is filtered by the MME according to an application ID. The page is filtered by the MME according to a UE subscription. The page is filtered by an eNB. The page is filtered by the eNB according to a paging priority. A barred application is blocked.

A communication network includes a plurality of operators, and the rule is associated with an operator of the plurality of operators. The plurality of operators includes a host operator and a hosted operator. The host operator requests the hosted operator to update the rule. The rule is provided with an index. The rule is selected according to the index. A CN selects the rule according to the index. The CN selects the rule according to a level of congestion. An ANDSF selects the rule according to the index.

Access is permitted or barred according to location information of the UE. The location information includes cell identification. The location information includes a GPS coordinate. A filter is provided for filtering communication network traffic. A packet filter is provided for filtering communication network traffic. A TFT is provided for filtering communication network traffic. The filter further includes a filter attribute. The filter attribute includes an allow attribute for permitting access. The filter attribute includes a block attribute for barring access. A UE is provided for performing the disclosed operations. A communication network is provided for providing all of the disclosed operations.

The UE includes a receiver and an application classification of the application is received. The application classification is received from a home network. The application classification is received from a visited network. The determined application class includes a preconfigured application class. The rule includes a list of applications further and access by the application is permitted or barred according to a comparison of the determined application class with the applications of the list of applications rule.

References which may be related to the foregoing disclosure may include: SP-130124, WID proposal for Application and Service Access Control (ASAC), SA #59; S1-131285, CR(0193) to 22.011; S1-131279, CR(0194) to 22.011; 3GPP TR 23.705, v0.2.0; 3GPP TR 22.806, v0.2.0; 3GPP TS 36.331, v11.0.0; 3GPP TS 23.402, v11.4.0; 3GPP TR 22.986, v11.0.0; SP-120546, WID proposal for application specific congestion control for data communication (FS_ACDC), SA #57, and 3GPP TS 22.011, V11.2.0.

Although the features and elements of the present invention are described in the preferred embodiments in particular combinations, each feature or element can be used alone without the other features and elements of the preferred embodiments or in various combinations with or without other features and elements of the present invention.

What is claimed is:

1. A wireless transmit/receive unit (WTRU) comprising:
a processor and memory, wherein the processor and the memory are configured to:
receive a non-access stratum (NAS) message, the NAS message comprising application access control classification information for the WTRU, wherein the application access control classification information indicates that a first application is associated with a first application class for application-based access class barring based on a first combination of a first application identifier associated with the first application and at least one application specific parameter associated with the first application, wherein the at least one application specific parameter associated with the first application corresponds to a characteristic of the first application, and the application access control classification information indicates that a second application is associated with a second application class for application-based access class barring based on a second combination of a second application identifier associated with the second application and at least one application specific parameter associated with the second application, wherein the at least one application specific parameter associated with the second application corresponds to a characteristic of the second application;
receive a system information broadcast, the system information broadcast indicating that at least a first application-based access control rule is activated in a cell for the first application class and a second application-based access control rule is activated in the cell for the second application class;
determine that accessing the cell to communicate data associated with the first application is allowed based on the first application-based access control rule indicated by the system information broadcast and the association of the first application with the first application class based on the first combination of the first application identifier and the application specific parameter associated with the second first application indicated by the NAS message; and determine that accessing the cell to communicate data associated with the second application is barred based on the second application-based access control rule indicated by the system information broadcast and the association of the second application with the second application class based on the second combination of the second application identifier and the application specific parameter associated with the second application indicated by the NAS message.

2. The WTRU of claim 1, wherein the NAS message indicates a first priority associated with the first application class.

3. The WTRU of claim 1, wherein the first application-based access control rule indicated in the system information broadcast is specific to a public land mobile network (PLMN).

4. The WTRU of claim 3, wherein the system information broadcast further indicates for which PLMN the first application-based access control rule and second application-based access control rule are activated.

5. The WTRU of claim 3, wherein the PLMN is a home PLMN (HPLMN), a visited PLMN (VPLMN), or a PLMN equivalent to a HPLMN.

6. The WTRU of claim 3, wherein the PLMN is a first PLMN and the WTRU stops and stores the application access control classification information specific to the first PLMN upon receiving application access control classification information specific to a second PLMN.

7. The WTRU of claim 3, wherein the PLMN provides definitions for the first application identifier associated with the first application and at least one application specific parameter associated with the first application and the second application identifier associated with the second application and at least one application specific parameter associated with the second application.

8. The WTRU of claim 7, wherein the WTRU stores the definitions and a PLMN identity of the PLMN that provided the definitions.

9. A wireless transmit/receive unit (WTRU) comprising:
a processor and memory, wherein the processor and the memory are configured to:
receive a non-access stratum (NAS) message, the NAS message comprising application access control classification information for the WTRU, wherein the application access control classification information indicates that a first application is associated with a first application class for application-based access class barring based on a first application server address information associated with the first application, and the application access control classification information indicates that a second application is associated with a second application class for application-based access class barring based on a second application server address information associated with the second application;
receive a system information broadcast, the system information broadcast indicating that at least a first application-based access control rule is activated in a cell for the first application class and a second application-based access control rule is activated in the cell for the second application class;
determine that accessing the cell to communicate data associated with the first application is allowed based on the first application-based access control rule indicated by the system information broadcast and the association of the first application with the first application class based on the first application server address information associated with the first application indicated by the NAS message; and
determine that accessing the cell to communicate data associated with the second application is barred based on the second application-based access control rule indicated by the system information broadcast and the association of the second application with the second application class based on the second application server address information associated with the second application indicated by the NAS message.

10. The WTRU of claim 9, wherein the application access control classification information further indicates that the first application is associated with the first application class for application-based access class barring based on a first combination of a first application identifier associated with the first application and at least one application specific parameter associated with the first application, wherein the at least one application specific parameter associated with the first application corresponds to a characteristic of the first application.

11. The WTRU of claim 9, wherein the application access control classification information further indicates that the second application is associated with the second application class for application-based access class barring based on a second combination of a second application identifier associated with the second application and at least one application specific parameter associated with the second application, wherein the at least one application specific parameter associated with the second application corresponds to a characteristic of the second application.

12. The WTRU of claim 9, wherein the NAS message indicates a first priority associated with the first application class.

13. The WTRU of claim 9, wherein the first application-based access control rule indicated in the system information broadcast is specific to a public land mobile network (PLMN).

14. The WTRU of claim 13, wherein the system information broadcast further indicates for which PLMN the first application-based access control rule and second application-based access control rule are activated.

15. The WTRU of claim 13, wherein the PLMN is a home PLMN (HPLMN), a visited PLMN (VPLMN), or a PLMN equivalent to a HPLMN.

16. The WTRU of claim 13, wherein the PLMN is a first PLMN and the WTRU stops and stores the application access control classification information specific to the first PLMN upon receiving application access control classification information specific to a second PLMN.

17. The WTRU of claim 13, wherein the PLMN provides definitions for the first application identifier associated with the first application and at least one application specific parameter associated with the first application and the second application identifier associated with the second application and at least one application specific parameter associated with the second application.

18. The WTRU of claim 17, wherein the WTRU stores the definitions and a PLMN identity of the PLMN that provided the definitions.

19. A wireless transmit/receive unit (WTRU) comprising a processor and memory, wherein the processor and the memory are configured to:
  receive a non-access stratum (NAS) message, the NAS message comprising application access control classification information for the WTRU, wherein the application access control classification information indicates that a first application is associated with a first application class for application-based access class barring based on a first combination of a first application identifier associated with the first application and a first application-related information associated with the first application, and the application access control classification information indicates that a second application is associated with a second application class for application-based access class barring based on a second combination of a second application identifier associated with the second application and a second application-related information associated with the second application;
  receive a system information broadcast, the system information broadcast indicating that at least a first application-based access control rule is activated in a cell for the first application class and a second application-based access control rule is activated in the cell for the second application class; and
  determine whether or not to access the cell to communicate data associated with at least one of the first application or the second application, wherein the determination of whether or not to access the cell is in accordance with the first application-based access control rule if the data is associated with the first application, and the determination of whether or not to access the cell is in accordance with the second application-based access control rule if the data is associated with the second application.

20. The WTRU of claim 19, wherein the NAS message indicates a first priority associated with the first application class.

* * * * *

UNITED STATES PATENT AND TRADEMARK OFFICE
CERTIFICATE OF CORRECTION

PATENT NO. : 12,382,333 B2  
APPLICATION NO. : 17/953612  
DATED : August 5, 2025  
INVENTOR(S) : Guanzhou Wang et al.

Page 1 of 1

It is certified that error appears in the above-identified patent and that said Letters Patent is hereby corrected as shown below:

In the Claims

In Claim 1: Column 27, Line 60, delete "second first" and insert --first--.

Signed and Sealed this  
Fourteenth Day of October, 2025

John A. Squires  
*Director of the United States Patent and Trademark Office*